US012728424B2

(12) United States Patent
Shin et al.

(10) Patent No.: US 12,728,424 B2
(45) Date of Patent: Sep. 8, 2026

(54) ELECTROSTATIC PRECIPITATOR AND CONTROL METHOD THEREOF

(71) Applicant: SAMSUNG ELECTRONICS CO., LTD., Suwon-si (KR)

(72) Inventors: Joonoh Shin, Suwon-si (KR); Myungsoo Kang, Suwon-si (KR); Hyongsoo Noh, Suwon-si (KR); Myungseob Song, Suwon-si (KR); Kyuho Shin, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 801 days.

(21) Appl. No.: 17/944,545

(22) Filed: Sep. 14, 2022

(65) Prior Publication Data

US 2023/0149948 A1 May 18, 2023

Related U.S. Application Data

(63) Continuation of application No. PCT/KR2022/013027, filed on Aug. 31, 2022.

(30) Foreign Application Priority Data

Nov. 17, 2021 (KR) ........................ 10-2021-0158549
Feb. 22, 2022 (KR) ........................ 10-2022-0023259

(51) Int. Cl.
*B03C 3/47* (2006.01)
*A61L 9/22* (2006.01)
(Continued)

(52) U.S. Cl.
CPC ................ *B03C 3/47* (2013.01); *B03C 3/011* (2013.01); *B03C 3/08* (2013.01); *B03C 3/09* (2013.01);
(Continued)

(58) Field of Classification Search
CPC .... B03C 3/47; B03C 3/68; B03C 3/70; B03C 3/00; B03C 2201/00; B03C 3/011;
(Continued)

(56) References Cited

U.S. PATENT DOCUMENTS 6,635,106 B2 10/2003 Katou et al.
10,537,901 B2 1/2020 Lee
(Continued)

FOREIGN PATENT DOCUMENTS

CN 102218373 A 10/2011
JP 2529030 8/1996
(Continued)

OTHER PUBLICATIONS

Extended European Search Report issued Oct. 15, 2024 for European Patent Application No. 22895804.7.
(Continued)

*Primary Examiner* — In Suk C Bullock
(74) *Attorney, Agent, or Firm* — STAAS & HALSEY LLP

(57) ABSTRACT

An electrostatic precipitator includes a dust collecting sheet configured to emit ions and configured to collect an aerosol charged by the ions, a power supplier electrically connected to the dust collecting sheet, a plate-shaped structure arranged upstream of an air flow path rather than the dust collecting sheet, and including at least one of a filter mesh or a grille including a plurality of openings, a potential stabilizer arranged between the plate-shaped structure and a ground, and configured to stabilize a potential of the plate-shaped structure, and a controller configured to control the power supplier to supply power to the dust collecting sheet.

14 Claims, 33 Drawing Sheets

(51) Int. Cl.

| | |
|---|---|
| ***B01D 46/00*** | (2022.01) |
| ***B01D 53/32*** | (2006.01) |
| ***B03C 3/00*** | (2006.01) |
| ***B03C 3/011*** | (2006.01) |
| ***B03C 3/08*** | (2006.01) |
| ***B03C 3/09*** | (2006.01) |
| ***B03C 3/12*** | (2006.01) |
| ***B03C 3/38*** | (2006.01) |
| ***B03C 3/41*** | (2006.01) |
| ***B03C 3/68*** | (2006.01) |
| ***B03C 3/70*** | (2006.01) |
| ***F01N 3/01*** | (2006.01) |
| ***F24F 1/0076*** | (2019.01) |
| ***F24F 8/192*** | (2021.01) |
| ***F24F 8/30*** | (2021.01) |

(52) U.S. Cl.

CPC .................. *B03C 3/12* (2013.01); *B03C 3/38* (2013.01); *B03C 3/41* (2013.01); *B03C 3/68* (2013.01); *B03C 3/70* (2013.01); *F24F 8/192* (2021.01); *F24F 8/194* (2021.01); *A61L 9/22* (2013.01); *B01D 46/0032* (2013.01); *B01D 53/323* (2013.01); *B03C 3/00* (2013.01); *B03C 2201/00* (2013.01); *F01N 3/01* (2013.01); *F23J 2217/102* (2013.01); *F24F 1/0076* (2019.02); *F24F 8/30* (2021.01)

(58) Field of Classification Search

CPC .... B03C 3/09; B03C 3/12; B03C 3/38; B03C 3/60; B03C 3/08; B03C 3/41; B03C 3/66; B03C 2201/04; B03C 2201/08; F24F 8/192; F24F 8/194; F24F 8/30; A61L 9/22; B01D 46/0032; B01D 53/323; F01N 3/01; F23J 2217/102

See application file for complete search history.

(56) References Cited

U.S. PATENT DOCUMENTS

| | | | | |
|---|---|---|---|---|
| 10,766,039 | B2 | 9/2020 | Yuge et al. | |
| 11,198,138 | B2 | 12/2021 | Shin et al. | |
| 2003/0005824 | A1 | 1/2003 | Katou et al. | |
| 2006/0018810 | A1* | 1/2006 | Taylor | B03C 3/68 422/186.04 |
| 2008/0190295 | A1* | 8/2008 | Reyes | B03C 3/68 96/82 |
| 2010/0147151 | A1 | 6/2010 | Ji et al. | |
| 2011/0185905 | A1 | 8/2011 | Ji et al. | |
| 2012/0312170 | A1* | 12/2012 | Noh | B03C 3/86 96/100 |
| 2017/0341087 | A1 | 11/2017 | Yuge et al. | |
| 2020/0023379 | A1* | 1/2020 | Shin | B03C 3/09 |
| 2020/0197953 | A1 | 6/2020 | Metzger et al. | |

FOREIGN PATENT DOCUMENTS

| | | |
|---|---|---|
| JP | 2001-96193 | 4/2001 |
| | 202280050458.0 | |
| JP | 2006-21077 | 1/2006 |
| JP | 3976611 | 9/2007 |
| JP | 2010-29839 | 2/2010 |
| JP | 2010-51866 | 3/2010 |
| JP | 4529386 | 8/2010 |
| JP | 2011-16056 | 1/2011 |
| JP | 4973335 | 7/2012 |
| JP | 2012-154621 | 8/2012 |
| JP | 5036607 | 9/2012 |
| JP | 5056475 | 10/2012 |
| JP | 5089000 | 12/2012 |
| JP | 5143815 | 2/2013 |
| JP | 5369210 | 12/2013 |
| JP | 2015-97443 | 5/2015 |
| JP | 2015-188832 | 11/2015 |
| JP | 2015-188851 | 11/2015 |
| JP | 2020-69446 | 5/2020 |
| KR | 10-2005-0029014 | 3/2005 |
| KR | 10-2005-0099165 | 10/2005 |
| KR | 10-2011-0088742 | 8/2011 |
| KR | 10-1453499 | 10/2014 |
| KR | 10-2016-0006062 | 1/2016 |
| KR | 10-2016-0076452 | 6/2016 |
| KR | 10-2019-0005443 | 1/2019 |
| KR | 10-2019-0065872 | 6/2019 |
| KR | 10-2019-00134362 | 12/2019 |
| KR | 10-2020-0010904 | 1/2020 |
| KR | 10-2022-0150528 | 11/2022 |
| KR | 10-2534790 | 5/2023 |
| WO | WO 2018/033172 A1 | 2/2018 |

OTHER PUBLICATIONS

International Search Report dated Dec. 27, 2022 in International Patent Application No. PCT/KR2022/013027 (3 pages; 3 pages English translation).

PCT/ISA/237 dated Dec. 27, 2022 in International Patent Application No. PCT/KR2022/013027 (5 pages).

Korean Office Action issued Mar. 27, 2026 for Application No. 202280050458.0.

* cited by examiner

ELECTROSTATIC PRECIPITATOR AND CONTROL METHOD THEREOF

CROSS-REFERENCE TO RELATED APPLICATION(S)

This application is a continuation application, under 35 U.S.C. § 111(a), of International Application No. PCT/KR2022/013027, filed on Aug. 31, 2022, which claims priority to Korean Patent Application No. 10-2021-0158549, filed on Nov. 17, 2021, and Korean Patent Application No. 10-2022-0023259, filed on Feb. 22, 2022 in the Korean Intellectual Property Office, the disclosure of which is incorporated by reference herein in their entireties.

BACKGROUND

1. Field

The disclosure relates to an electrostatic precipitator including a dust collecting sheet configured to generate ions and collect aerosols in air, and a structure provided to diffuse the ions.

2. Description of Related Art

High concentrations of aerosol in homes, rooms, shopping malls, factories, and offices may cause health problems. These aerosols may be generated by smoking, cooking, cleaning, welding, grinding, etc. in confined spaces. An electrostatic precipitator corresponding to a device for removing such aerosols may be used in an air purifier or an air conditioner having an air purifying function.

In general, an electrostatic precipitator may include a charging unit configured to positively (+) or negatively (−) charge aerosols contained in the air, through the electric discharge, and a dust collecting unit configured to collect the aerosol charged by the charging unit. In a conventional electrostatic precipitator, a charging unit and a dust collecting unit are provided separately. Therefore, a lot of components are required and a process of assembling each component is needed, which causes an increase in a thickness of the electrostatic precipitator.

In addition, the conventional electrostatic precipitator is not provided with a structure for diffusing ions generated by the charging unit.

SUMMARY

In accordance with an aspect of the disclosure, an electrostatic precipitator includes a dust collecting sheet configured to emit ions and configured to collect an aerosol charged by the ions from air flowing along an air flow path through the electrostatic precipitator, a power supplier electrically connectable to the dust collecting sheet, a plate-shaped structure arranged upstream of the dust collecting along the air flow path, the plate-shaped structure including at least one of a filter mesh or a grille including a plurality of openings, a potential stabilizer arranged between the plate-shaped structure and a ground, and configured to stabilize a potential of the plate-shaped structure, and a controller configured to control the power supplier to supply power to the dust collecting sheet.

The potential stabilizer may include a relay configured to connect or disconnect the plate-shaped structure and the ground, and the controller may be configured to control opening or closing of the relay based on a predetermined period.

The controller may be configured to set a closing time to be less than an opening time of the relay.

The potential stabilizer may further include a resistor-capacitor (RC) circuit connectable to the plate-shaped structure and connectable in parallel to the relay.

The potential stabilizer may include a resistance element.

The plate-shaped structure may be formed of a conductive material.

The plate-shaped structure may be formed of a semi-conductive material having a uniform resistance, or the plate-shaped structure may include a first member formed of an insulator and a second member formed of a conductive material or a semi-conductive material.

The electrostatic precipitator may further include a conductive member arranged on at least a portion of a rim of the plate-shaped structure.

The conductive member may include a bent shape to surround the rim of the plate-shaped structure.

The conductive member may be formed between the filter mesh and the grille.

The plate-shaped structure may be formed in a quadrangle, and the conductive member may be arranged on a first side of the plate-shaped structure and a second side of the plate-shaped structure facing the first side symmetrically.

The plate-shaped structure may be formed in a quadrangle, and the conductive member may include a first conductive member arranged adjacent to a first vertex of the plate-shaped structure and a second conductive member arranged adjacent to a second vertex of the plate-shaped structure arranged diagonally with respect to the first vertex, A first length of the first conductive member and a second length of the second conductive member may be less than a length of one side of the plate-shaped structure.

The electrostatic precipitator may further include an insulating member arranged outside the conductive member to cover the conductive member.

The dust collecting sheet may include a plurality of high-voltage electrodes including a first dielectric layer and a first conductive electrode layer in which a part thereof is exposed to an outside through an opening of the first dielectric layer; the plurality of high-voltage electrodes to which a high-voltage is applied, and a plurality of low-voltage electrodes including a second dielectric layer and a second conductive electrode layer printed on an inside of the second dielectric layer, the plurality of low-voltage electrodes alternately arranged with the plurality of high voltage electrodes and to which a low-voltage is applied.

In accordance with another aspect of the disclosure, a control method of an electrostatic precipitator including a dust collecting sheet configured to collect an aerosol charged by the ions from air flowing along an air flow path through the electrostatic precipitator and a filter assembly arranged upstream of the dust collecting sheet along the air flow path, the control method includes controlling a power supplier to supply power to the dust collecting sheet, opening a relay of a potential stabilizer arranged between the filter assembly and a ground based on the power being supplied to the dust collecting sheet, and controlling the relay to be repeatedly opened or closed based on a predetermined period.

A closing time of the relay may be set to be less than an opening time of the relay.

In accordance with another aspect of the disclosure, an electrostatic precipitator includes a dust collecting sheet configured to emit ions and configured to collect an aerosol charged by the ions, a power supplier electrically connected to the dust collecting sheet, a plate-shaped structure arranged upstream of an air flow path rather than the dust collecting sheet, and including at least one of a filter mesh or a grille including a plurality of openings, a conductive member arranged on at least a portion of a rim of the plate-shaped structure, and a resistance element arranged between the conductive member and a ground, and configured to stabilize a potential of the plate-shaped structure.

The plate-shaped structure may be formed of a semi-conductive material having a uniform resistance as a whole, or the plate-shaped structure may include a first member formed of an insulator and a second member formed of a conductive material or a semi-conductive material.

The conductive member may include a bent shape to surround the rim of the plate-shaped structure.

The conductive member may be formed between the filter mesh and the grille.

BRIEF DESCRIPTION OF THE DRAWINGS

The above and other aspects, features, and advantages of certain embodiments of the present disclosure will become apparent from the following description taken in conjunction with the accompanying drawings of which:

FIG. 1 is a view illustrating an electrostatic precipitator according to an embodiment of the disclosure;

FIG. 5 is a view illustrating a high-voltage electrode according to a first embodiment;

FIG. 11D is a view illustrating an operation of the relay provided in the electrostatic precipitator according to an embodiment of the disclosure;

FIG. 13 is a view illustrating an additional embodiment of the electrostatic precipitator further including a resistor-capacitor (RC) circuit;

FIG. 15 is a view schematically illustrating an electrostatic precipitator including an ion emitter, according to another embodiment;

FIG. 24 is a view illustrating an electrostatic precipitator according to still another embodiment of the disclosure;

DETAILED DESCRIPTION

Figure 2:
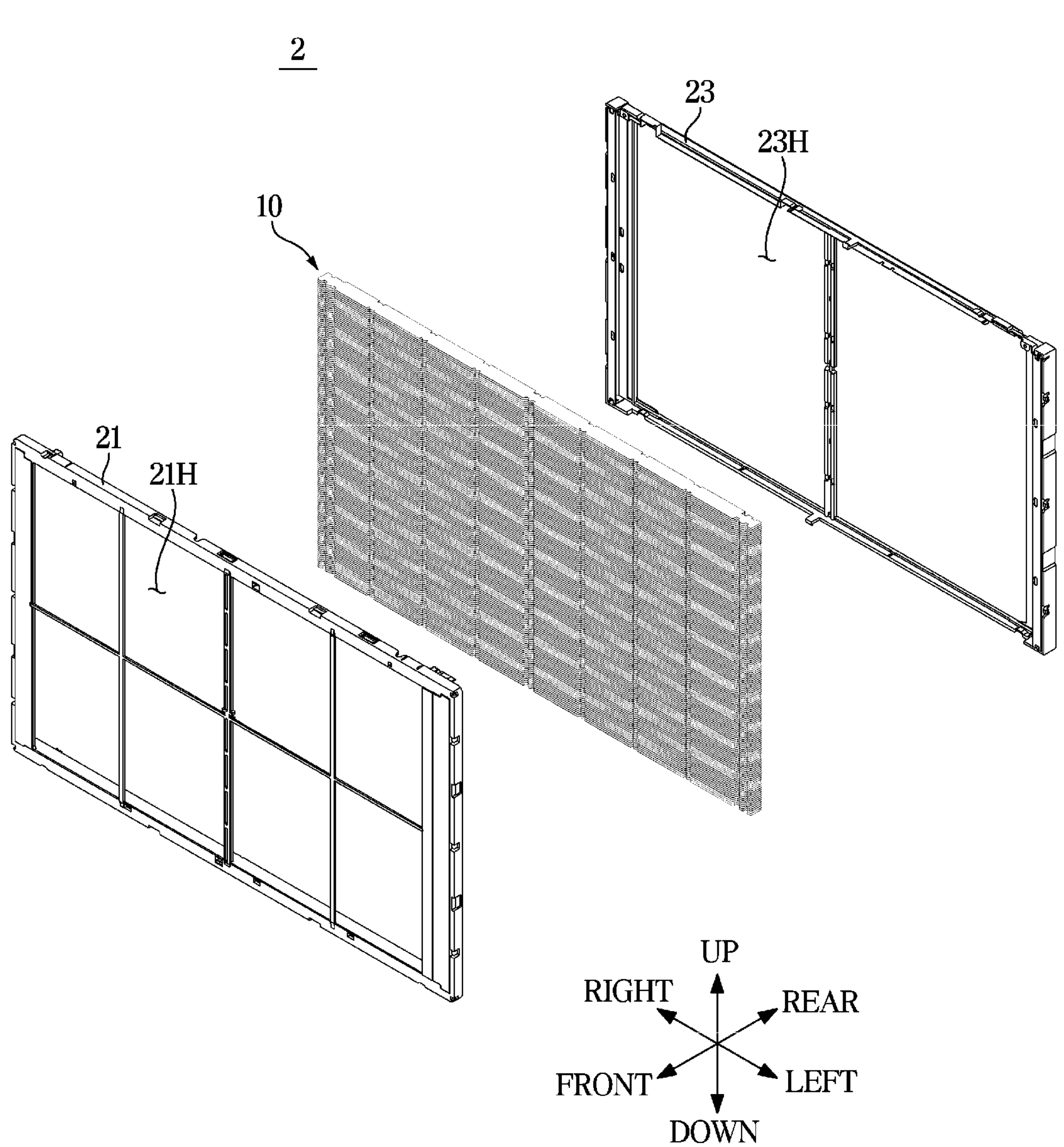
FIG. 2 is an exploded view illustrating a dust collection assembly according to an embodiment of the disclosure.

Embodiments described in the disclosure and configurations shown in the drawings are merely examples of the embodiments of the disclosure, and may be modified in various different ways at the time of filing of the present application to replace the embodiments and drawings of the disclosure. In addition, the same reference numerals or signs shown in the drawings of the disclosure indicate elements or components performing substantially the same function.

Also, the terms used herein are used to describe the embodiments and are not intended to limit and/or restrict the disclosure. The singular forms "a," "an" and "the" are intended to include the plural forms as well, unless the context clearly indicates otherwise. In this disclosure, the terms "including", "having", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, but elements are not limited by these terms. These terms are only used to distinguish one element from another element. For example, without departing from the scope of the disclosure, a first element may be termed as a second element, and a second element may be termed as a first element. The term of "and/or" includes a plurality of combinations of relevant items or any one item among a plurality of relevant items.

In the following detailed description, the terms of "front end", "rear end", "upper portion", "lower portion", "front surface", "rear surface", "upper end", "lower end" and the like may be defined by the drawings, but the shape and the location of the component is not limited by the term.

It will be understood that when an element is referred to as being "connected" another element, it can be directly or indirectly connected to the other element, wherein the indirect connection includes "connection via a wireless communication network" or "connection via another part".

In the following description, terms such as "unit", "part", "block", "member", and "module" indicate a unit for processing at least one function or operation. For example, those terms may refer to at least one process processed by at least one hardware such as Field Programmable Gate Array (FPGA), Application Specific Integrated Circuit (ASIC), at least one software stored in a memory or a processor.

An identification code is used for the convenience of the description but is not intended to illustrate the order of each step. The each step may be implemented in the order different from the illustrated order unless the context clearly indicates otherwise.

Therefore, it is an aspect of the disclosure to provide an electrostatic precipitator including a structure provided to diffuse ions generated by a dust collecting sheet.

It is another aspect of the disclosure to provide an electrostatic precipitator and a control method thereof capable of providing a potential stabilizer configured to stabilize an electric potential, between a structure provided to diffuse ions and a ground, so as to allow an electric discharge to be smoothly performed in a high voltage electrode of a dust collecting sheet and simultaneously, to prevent the ions from accumulating on the structure.

Additional aspects of the disclosure will be set forth in part in the description which follows and, in part, will be obvious from the description, or may be learned by practice of the disclosure.

Hereinafter an embodiment according to the disclosure will be described in detail with reference to the accompanying drawings.

Figure 1:
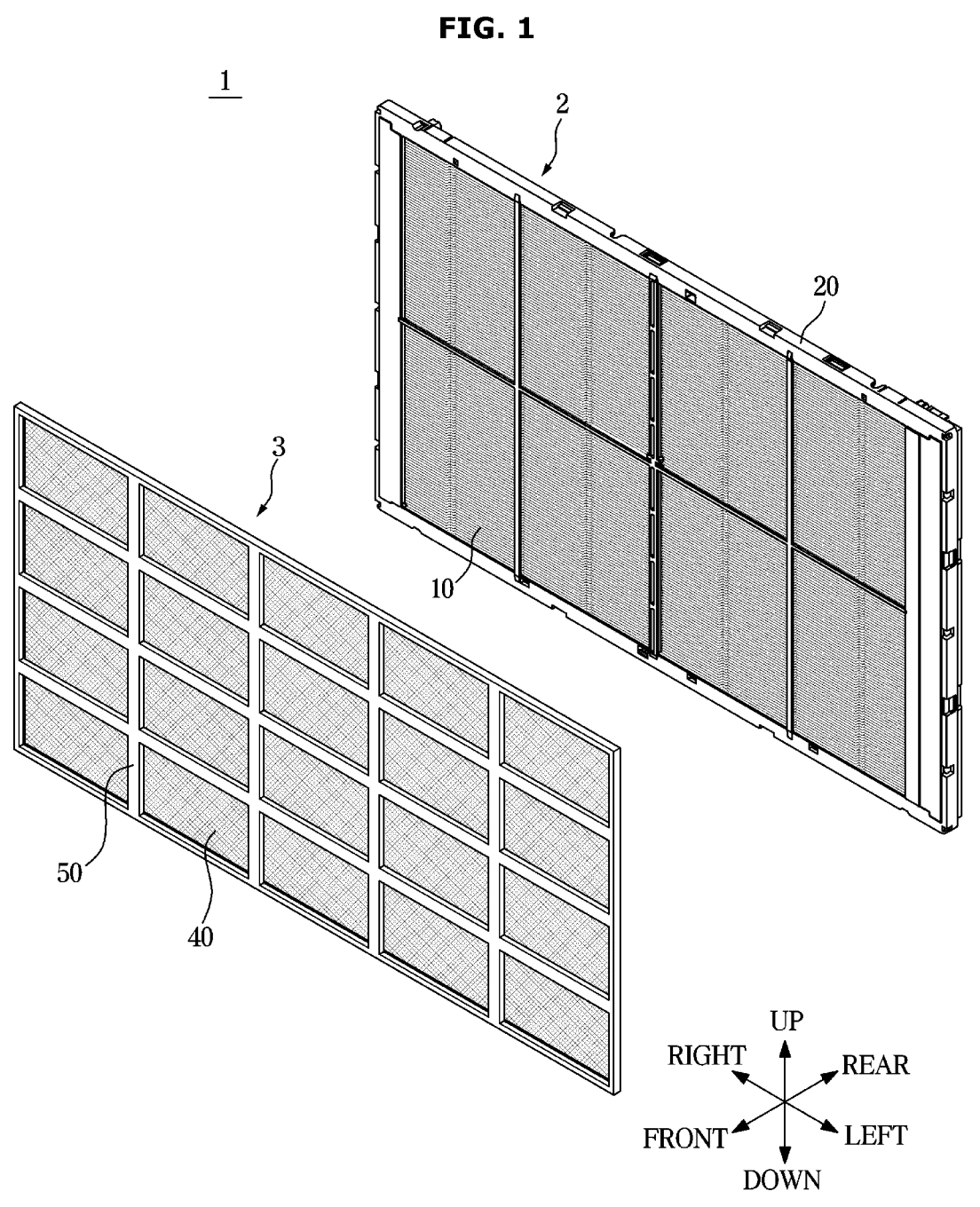
Figure 3:
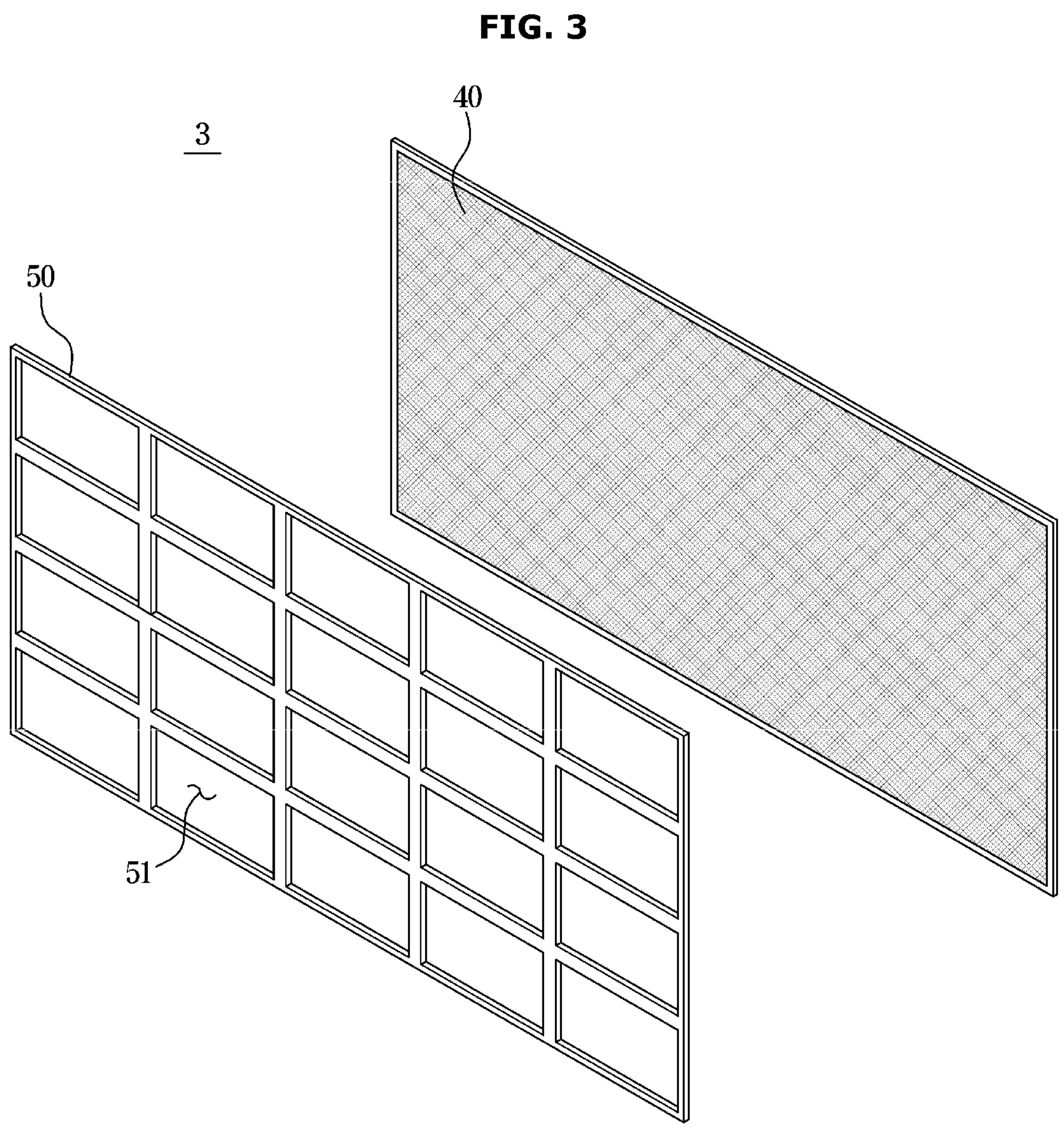
FIG. 3 is an exploded view illustrating a filter assembly according to an embodiment of the disclosure.

FIG. 1 is a view illustrating an electrostatic precipitator according to an embodiment of the disclosure. FIG. 2 is an exploded view illustrating a dust collection assembly according to an embodiment of the disclosure. FIG. 3 is an exploded view illustrating a filter assembly according to an embodiment of the disclosure.

An electrostatic precipitator is an apparatus configured to remove an aerosol generated by activities such as smoking, cooking, cleaning, welding, grinding, etc. in confined spaces. The electrostatic precipitator 1 may be installed inside a device capable of performing an air filtering function, such as an air conditioner or an air purifier.

An air purifier or air conditioner (not shown) may include an inlet (not shown) through which external air is introduced, the electrostatic precipitator 1 configured to filter the air introduced through the inlet, a blower fan (not shown) configured to move the air, and an outlet (not shown) through which air filtered by a filter member is discharged. By an operation of the blower fan, air may flow through the inlet, the electrostatic precipitator 1, and the outlet.

An apparatus such as an air purifier or air conditioner may include various filter devices in addition to the electrostatic precipitator 1. For example, a fine dust collecting filter in the form of a non-woven fabric formed of polypropylene resin or polyethylene resin and/or a granular activated carbon filter may optionally be provided.

Referring to FIG. 1, the electrostatic precipitator 1 may include a dust collection assembly 2 and a filter assembly 3. The dust collection assembly 2 and the filter assembly 3 may be spaced apart from each other. It may be appropriate that the filter assembly 3 is arranged to be spaced apart from the dust collection assembly 2 by a distance within a range of greater than or equal to 4 mm, but less than or equal to 10 mm.

Air may pass through the filter assembly 3 and then through the dust collection assembly 2. In other words, the filter assembly 3 may be arranged upstream of an air flow path than the dust collection assembly 2. For example, in a state in which the electrostatic precipitator 1 is arranged perpendicular to a ground surface and air flows from the front to the rear, the filter assembly 3 may be located in front of the dust collection assembly 2.

As another example, in a state in which the electrostatic precipitator 1 is arranged horizontally with the ground surface and air flows from the bottom to the top, the filter assembly 3 may be located below the dust collection assembly 2. An arrangement structure of the filter assembly 3 and the dust collection assembly 2 is not limited thereto. Various arrangement structures provided to allow air to pass through the filter assembly 3 first may be applied thereto.

Referring to FIGS. 1 and 2, the dust collection assembly 2 may include a dust collecting sheet 10 and a cover 20 provided to cover the dust collecting sheet 10. The cover 20 may include a frame shape surrounding an outer periphery of the dust collecting sheet 10. The cover 20 of the dust collection assembly 2 may include a first cover 21 and a second cover 23. The first cover 21 and the second cover 23 may be coupled to each other. The dust collecting sheet 10 may be provided between the first cover 21 and the second cover 23, and protected by the first cover 21 and the second cover 23.

In the state in which the dust collection assembly 2 is placed perpendicular to the ground surface, the first cover 21 may be arranged in front of the dust collecting sheet 10, and the second cover 23 may be arranged at the rear of the dust collecting sheet 10. Air may pass through the dust collecting sheet 10 through openings 21H and 23H formed inside each of the first cover 21 and the second cover 23.

Referring to FIGS. 1 and 3, the filter assembly 3 may include a plate-shaped structure. The plate-shaped structure may include at least one of a filter mesh 40 or a grille 50 including a plurality of openings 51.

In other words, the filter assembly 3 may be formed in a plate shape. The filter assembly 3 may include a shape corresponding to a shape of the dust collection assembly 2 (for example, quadrangle or circle). The filter mesh 40 and the grille 50 may be provided in a plate shape or in a shape corresponding to the shape of the dust collecting sheet 10. The plate-shaped structure may be formed of a conductive material or a semi-conductive material. In other words, the filter mesh 40 and the grille 50 may be formed of a conductive material or a semi-conductive material.

The filter mesh 40 and the grille 50 may be integrally formed with each other or formed to be detachable from each other. In the state in which the filter assembly 3 is placed perpendicular to the ground surface, the grille 50 may be arranged at the front or rear of the filter mesh 40. The grille 50 may protrude from a surface of the filter mesh 40. The grille 50 may support the filter mesh 40 and protect the filter mesh 40.

Figure 4:
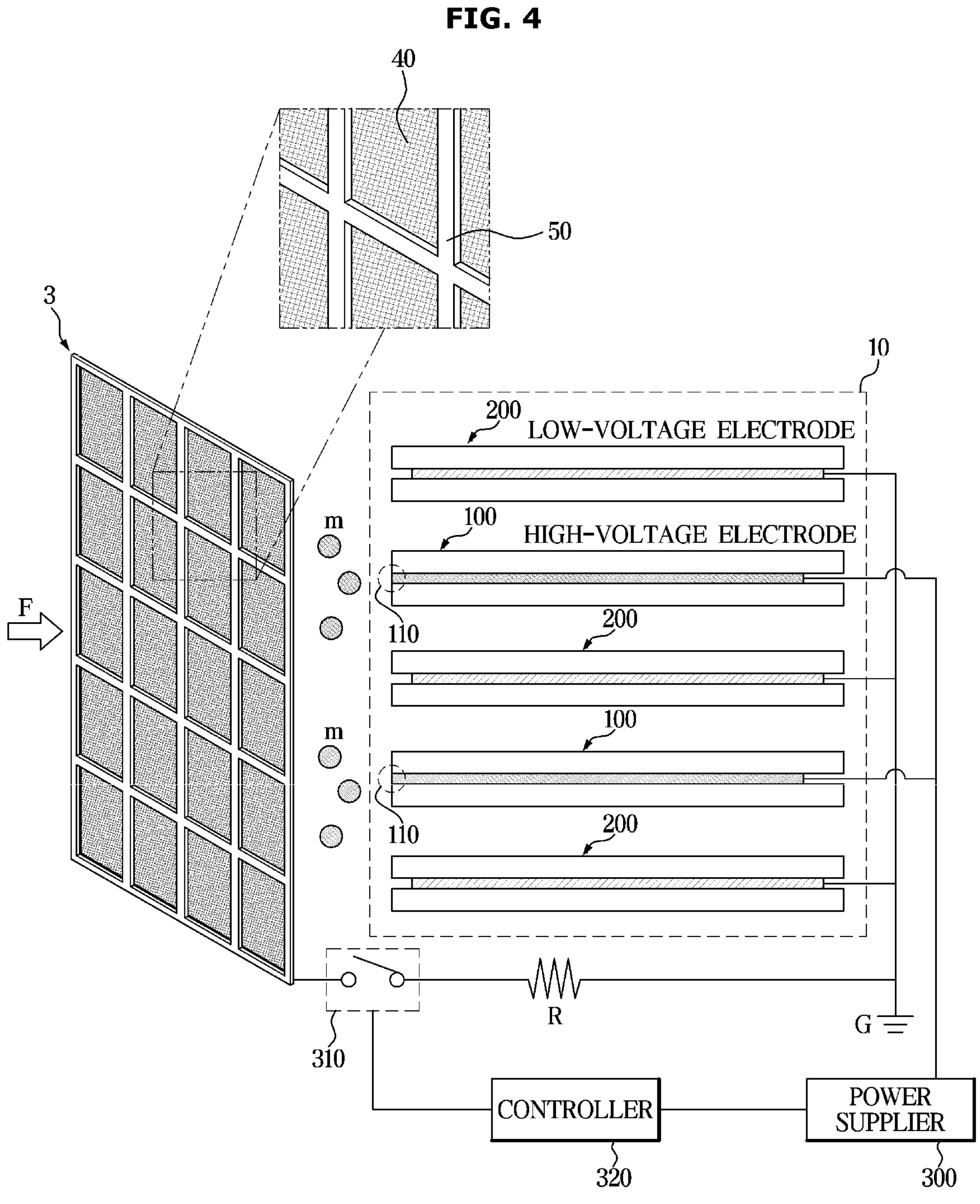
FIG. 4 is a view schematically illustrating configurations of the electrostatic precipitator according to an embodiment of the disclosure.
Figure 5:
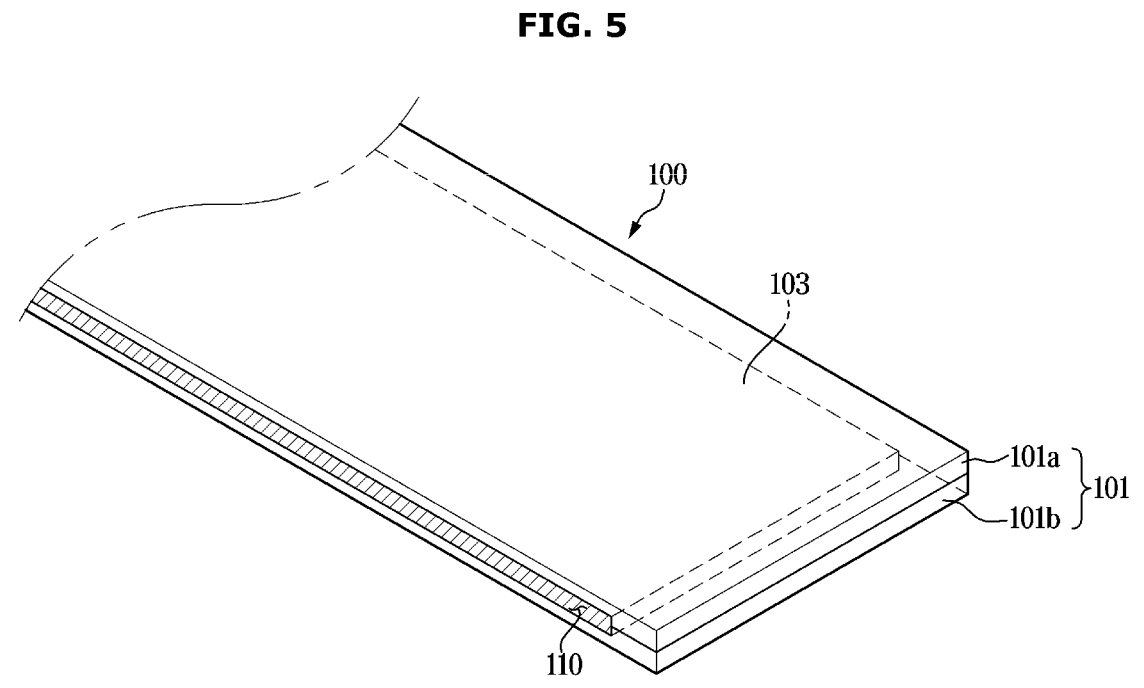
Figure 6:
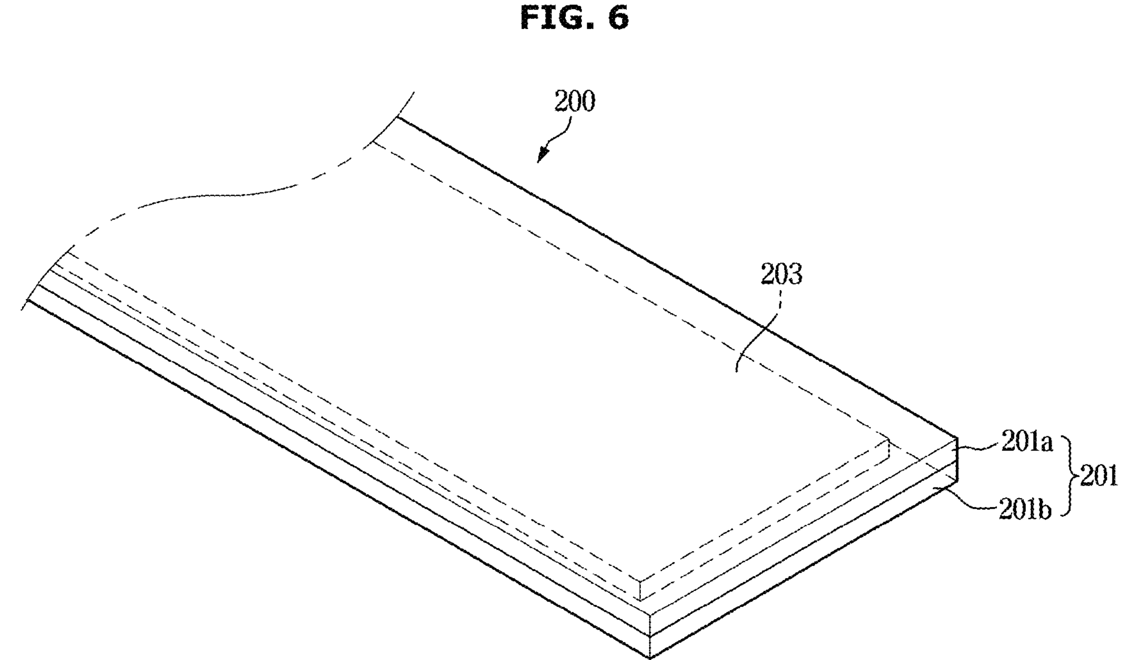
FIG. 6 is a view illustrating a low-voltage electrode according to a first embodiment.

FIG. 4 is a view schematically illustrating configurations of the electrostatic precipitator according to an embodiment of the disclosure. FIG. 5 is a view illustrating a high-voltage electrode according to a first embodiment. FIG. 6 is a view illustrating a low-voltage electrode according to a first embodiment.

Referring to FIGS. 4, 5 and 6, the dust collecting sheet 10 may be formed by stacking a plurality of electrodes 100 and 200. The dust collecting sheet 10 may include a high-voltage electrode 100 as a positive electrode and a low-voltage electrode 200 as a negative electrode. Each of the high-voltage electrode 100 and the low-voltage electrode 200 may be provided in plurality. The high-voltage electrode 100 and the low-voltage electrode 200 may be alternately arranged and stacked. The high-voltage electrode 100 may be arranged to have an appropriate distance from the low-voltage electrode 200 to prevent generation of spark between the high-voltage electrode 100 and the low-voltage electrode 200.

The dust collecting sheet 10 may be electrically connected to a power supplier 300. The power supplier 300 may apply a high voltage to the high-voltage electrode 100. The power supplier 300 may include various circuits configured to apply a voltage to the high-voltage electrode 100 and/or the low-voltage electrode 200. The low-voltage electrode 200 may be electrically connected to a ground (G), and a low voltage may be applied to the low-voltage electrode 200.

In response to a predetermined voltage being applied between the high-voltage electrode 100 and the low-voltage electrode 200, an electric field may be formed between the high-voltage electrode 100 as a positive electrode and the low-voltage electrode 200 as a negative electrode. The positive electrode may represent an electrode having a high potential level and the negative electrode may represent an electrode having a low potential level based on a potential difference.

The high-voltage electrode 100 may include a first dielectric layer 101 and a first conductive electrode layer 103 arranged inside the first dielectric layer 101. The first dielectric layer 101 may include a first upper dielectric layer 101*a* arranged in an upper side with respect to the first conductive electrode layer 103, and a first lower dielectric layer 101*b* arranged in a lower side with respect to the first conductive electrode layer 103.

Alternatively, the first dielectric layer 101 may be integrally formed without being divided into an upper portion and a lower portion. For example, the high-voltage electrode 100 may be manufactured by a double injection method in which the first dielectric layer 101 is injected by inserting a conductive material forming the first conductive electrode layer 103.

An opening 110 may be formed in the first dielectric layer 101 of the high-voltage electrode 100. A portion of the first conductive electrode layer 103 may be exposed to the outside through the opening 110. The opening 110 may be formed in a portion in which the first upper dielectric layer 101*a* and the first lower dielectric layer 101*b* are overlapped. The opening 110 may be formed to have a straight shape on one side of the first dielectric layer 101.

One side of the first dielectric layer 101 may be an upstream side of the first dielectric layer 101 with respect to a direction F in which air flows. In the first dielectric layer 101, the first conductive electrode layer 103 may be in close contact with the upstream side in which the opening 110 is formed. Accordingly, the first conductive electrode layer 103 may be exposed to the outside through the opening 110. The opening 110 may be formed not only on the upstream side of the first dielectric layer 101 but also on the downstream side.

The low-voltage electrode 200 may include a second dielectric layer 201 and a second conductive electrode layer 203 arranged inside the second dielectric layer 201. The second dielectric layer 201 may include a second upper dielectric layer 201*a* arranged in an upper side with respect to the second conductive electrode layer 203, and a second lower dielectric layer 201*b* arranged in a lower side with respect to the second conductive electrode layer 203. The second dielectric layer 201 may be integrally formed without being divided into an upper portion and a lower portion.

Air may pass through the filter assembly 3 and the dust collecting sheet 10 along the direction F. The air may be charged before reaching the dust collecting sheet 10. Air may be charged while passing through the filter assembly 3. The charged air may pass between the high-voltage electrode 100 and the low-voltage electrode 200.

The dust collecting sheet 10 may emit ions (m) to positively (+) or negatively (−) charge the aerosol in the air. The first conductive electrode layer 103 exposed to the outside through the opening 110 of the high-voltage electrode 100 may emit ions (m) into space. Air may be charged by contact with the released ions (m). The aerosol in the air may be positively (+) or negatively (−) charged. The opening 110 of the high-voltage electrode 100 may be referred to as a 'discharge unit'.

In response to an aerosol in the air being positively (+) charged, the aerosol may be attached to the low-voltage electrode 200 corresponding to a negative pole. In response to an aerosol in the air being negatively (−) charged, the aerosol may be attached to the high-voltage electrode 100 corresponding to a positive pole. Accordingly, the air passing through the electrostatic precipitator 1 may be discharged in a clean state from which the aerosol is removed.

Based on the air being charged by the ions (m) emitted through the opening 110 formed in the high-voltage electrode 100 of the dust collecting sheet 10, a separate discharge unit may not be required, and thus the electrostatic precipitator 1 may be manufactured to be slim. In addition, because the number of components of the electrostatic precipitator 1 is reduced, the manufacturing cost may also be reduced.

The filter assembly 3 composed of at least one of the filter mesh 40 or the grille 50 may filter out foreign substances (for example, dust) including a particle greater than a particle of the aerosol that is collected by the dust collecting sheet 10 of the dust collection assembly 2.

In a state in which the entire filter assembly 3 is formed of a non-conductive material, the non-conductive material may have dielectric properties, and thus dielectric polarization may occur in the filter assembly 3. In this case, ions (m) accumulate in the filter assembly 3 and the filter assembly 3 has a potential. Therefore, a potential difference between the high-voltage electrode 100 and the filter assembly 3 of the dust collecting sheet 10 is reduced, and thus an amount of charge of the aerosol flowing into the dust collecting sheet 10 is reduced, thereby reducing the collection efficiency of the aerosol.

In a state in which the entire of the filter assembly 3 is formed of a conductive material and the filter assembly 3 is connected to the ground G, ions (m) emitted from the high-voltage electrode 100 of the dust collecting sheet 10 may quickly escape to the ground through the filter assembly 3. A surface resistance of the conductive material may be less than $10^6$ [ohm/sq]. Therefore, the ions (m) may not be diffused into space, and an amount of charge of the aerosol in the air flowing into the dust collecting sheet 10 may be reduced. Accordingly, the collection efficiency of the aerosol is reduced. In addition, sparks may occur in response to the filter assembly 3 of conductive material being arranged adjacent to the high-voltage electrode 100.

Based on the filter assembly 3 being entirely formed of a semi-conductive material, a non-uniform electric field may be formed between a region adjacent to the ground G and a region far from the ground G in the surface of the filter assembly 3. In this case, more ions (m) emitted from the high-voltage electrode 100 may be collected in a partial region of the filter assembly 3. Accordingly, the amount of charge of the aerosol in the airflowing into the dust collecting sheet 10 may be reduced, and the collection efficiency of the aerosol may be reduced.

In the conventional manner, it does not take into account a difficulty caused by a fact that the filter mesh 40 and the grille 50 forming the filter assembly 3 are formed of a non-conductive material, a conductive material or a semi-conductive material.

To ease the difficulty, the disclosed electrostatic precipitator 1 may include a potential stabilizer arranged between the filter assembly 3 and the ground G and configured to stabilize an electric potential of the filter assembly 3. The potential stabilizer may be arranged between a plate-shaped structure provided with at least one of the filter mesh 40 or the grille 50, and the ground G. The potential stabilizer may include a relay 310 configured to connect or disconnect the plate-shaped structure and the ground G. That is, the relay 310 may be arranged between the plate-shaped structure provided with at least one of the filter mesh 40 or the grille 50, and the ground G. The relay 310 is a switch configured to be controlled by a controller 320, so as to be turned on or turned off.

The relay 310 may be opened or closed based on a predetermined period. In response to the relay 310 being opened, that is, in response to the relay 310 being turned off, the filter assembly 3 and the ground G are disconnected. In response to the relay 310 being opened, some of the ions (m) emitted from the high-voltage electrode 100 of the dust collecting sheet 10 may be diffused into an external space located on the upstream side than the filter assembly 3, and another part of the ions (m) may accumulate in the filter assembly 3. Therefore, even if the filter assembly 3 is formed of a conductive material, the ions (m) may accumulate in the filter assembly 3 in response to the relay 310 being opened. That is, even if the filter mesh 40 and the grille 50 forming the filter assembly 3 are formed of a conductive material, the ions (m) emitted from the dust collecting sheet 10 may be diffused into space through the filter assembly 3. Accordingly, the dust collection efficiency of the dust collecting sheet 10 may be increased.

In addition, even if the filter assembly 3 is formed of a semi-conductive material, the filter assembly 3 is not connected to the ground G in response to the relay 310 being opened. Therefore, the ions (m) may be evenly distributed in the surface region of the filter mesh 40 and the grille 50 formed of a semi-conductive material, and the ions (m) may be diffused from the entire surface region of the filter assembly 3 to the external space on the upstream side.

The electric potential of the filter assembly 3 may be increased while the relay 310 is opened for a predetermined time. Based on the potential difference between the filter assembly 3 and the high-voltage electrode 100 being reduced, the electric discharge may not be generated smoothly in the high-voltage electrode 100. In response to the relay 310 being closed, that is, in response to the relay 310 being turned on, the ions accumulating in the filter assembly 3 may escape to the ground G. Therefore, the potential difference between the filter assembly 3 and the high-voltage electrode 100 may be restored, and the electric discharge of the high-voltage electrode 100 may be generated smoothly again. For example, in response to the potential of the filter assembly 3 being equal to the potential of the high-voltage electrode 100, that is, a relative potential of the filter assembly 3 being 1 with respect to the potential of the high-voltage electrode 100, the ions accumulating in the filter assembly 3 may be removed by turning on the relay 310.

After the potential difference between the filter assembly 3 and the high-voltage electrode 100 is restored by closing the relay 310, the relay 310 may be re-opened to allow the ions to be diffused through the filter assembly 3.

A period of time in which the relay 310 is closed is set to be less than a period of time in which the relay 310 is opened. In other words, the closing time of the relay 310 is set to be less than the opening time of the relay 310. A ratio of the closing time (ON time) of the relay 310 to the predetermined period may be set to be less than or equal to 0.1. This is because in response to the relay 310 being turned on, the ions accumulating in the filter assembly 3 escape to the ground G within a relatively short time.

In addition, the potential stabilizer may include a resistance element R. For example, the resistance element R may be arranged between the relay 310 and the ground G. The resistance element R may prevent an excessive current from flowing through the filter assembly 3, and prevent sparks from being generated between the filter assembly 3 and the dust collecting sheet 10. In addition, the potential stabilizer implemented as the resistance element R may allow a rate, at which the ions escape through the ground G, to be relatively slow.

The controller 320 may control the operation of the electrostatic precipitator 1. The controller 320 may be electrically connected to the power supplier 300 and the relay 310 so as to control each of the power supplier 300 and the relay 310. The controller 320 may control the power supplier 300 to supply power to the dust collecting sheet 10 based on an operation start command of the electrostatic precipitator 1. In addition, the controller 320 may open or close the relay 310 based on the predetermined period.

The controller 320 may be implemented as a control circuit, provided in the electrostatic precipitator 1, or provided in an air conditioner or an air purifier in which the electrostatic precipitator 1 is installed. For example, in response to the start of the operation of the air conditioner or air purifier, the operation start command of the electrostatic precipitator 1 may be input.

The controller 320 may include a processor and a memory. The memory may memorize/store various information necessary for the operation of the electrostatic precipitator 1. The memory may store instructions, applications, data and/or programs necessary for the operation of the electrostatic precipitator 1. The processor may generate a control signal for controlling the operation of the electrostatic precipitator 1 based on instructions, applications, data and/or programs stored in the memory.

The memory may include a volatile memory such as static random access memory (S-RAM) or dynamic random access memory (D-RAM) for temporarily storing data. In addition, the memory may include a non-volatile memory such as Read Only Memory (ROM), Erasable Programmable Read Only Memory (EPROM), or Electrically Erasable Programmable Read Only Memory (EEPROM) for storing data for a long period of time.

The processor corresponding to hardware may include a logic circuit and an arithmetic circuit. The processor may process data according to a program and/or instructions provided from the memory, and may generate a control signal according to the processing result. The memory and the processor may be implemented as one control circuit or a plurality of circuits.

Figure 7:
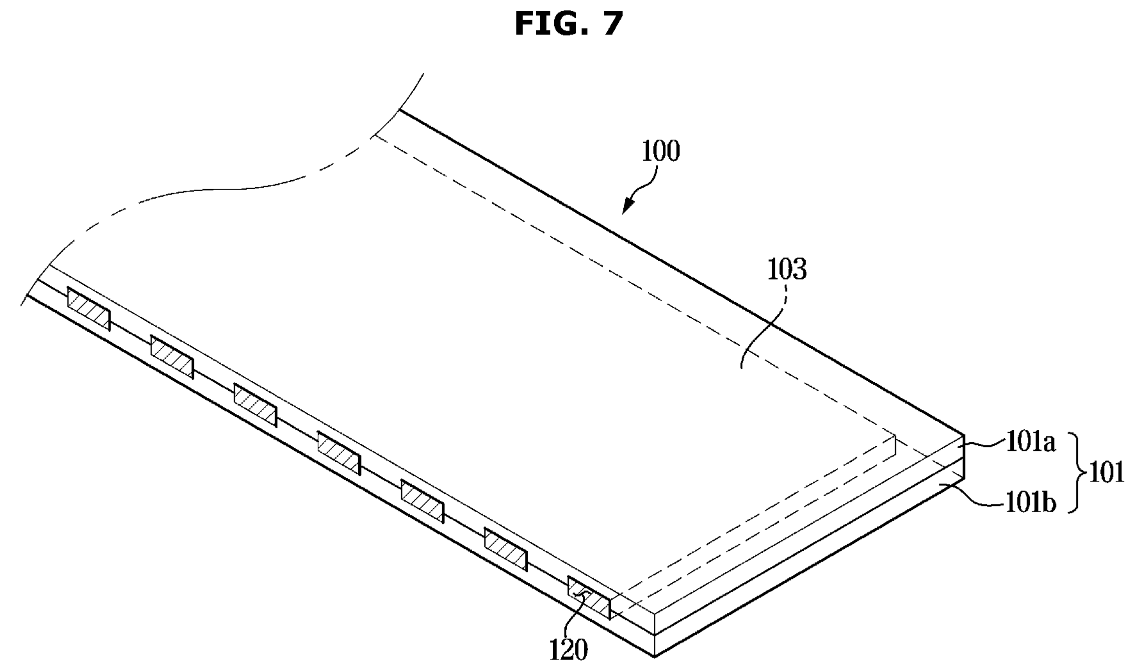
FIG. 7 is a view illustrating a high-voltage electrode according to a second embodiment.
Figure 8:
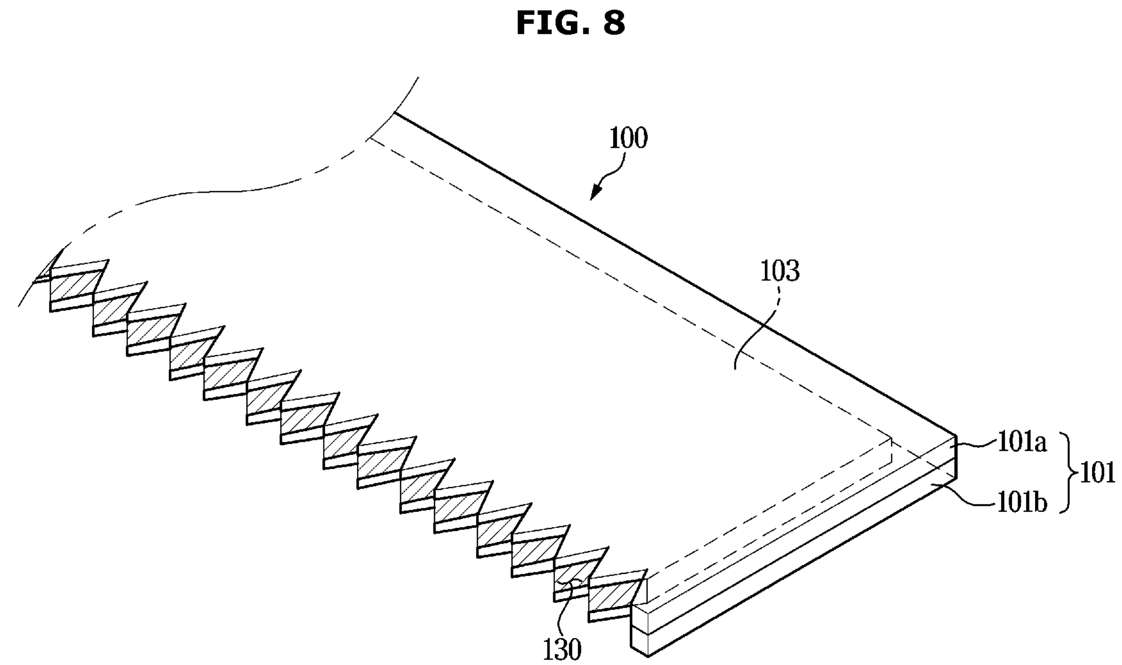
FIG. 8 is a view illustrating a high-voltage electrode according to a third embodiment.

FIG. 7 is a view illustrating a high-voltage electrode according to a second embodiment. FIG. 8 is a view illustrating a high-voltage electrode according to a third embodiment.

Referring to FIG. 7, a plurality of openings 120 having a straight shape may be formed on one side of a high-voltage electrode 100. The plurality of openings 120 may be formed on a portion in which a first upper dielectric layer 101*a* and a first lower dielectric layer 101*b* are overlapped. The plurality of openings 120 may be formed on an upstream side and/or downstream side of a first dielectric layer 101.

Referring to FIG. 8, an upstream side of a first conductive electrode layer 103 of the high-voltage electrode 100 may be formed in a sawtooth shape. Based on the direction F (refer to FIG. 4) in which the air flows, the upstream side of the first conductive electrode layer 103 of the high-voltage electrode 100 may be formed to protrude in the sawtooth shape. The upstream side of the first dielectric layer 101 may be formed to correspond to a shape of the first conductive electrode layer 103. That is, based on the direction F in which the air flows, the upstream side of the first dielectric layer 101 may be formed to protrude in the sawtooth shape. On the upstream side of the first dielectric layer 101, an opening 130 may be formed to allow the upstream side of the first conductive electrode layer 103 to be exposed to the outside. Because the first conductive electrode layer 103 exposed to the outside is formed in the sawtooth shape, energy may be concentrated. Alternatively, the opening 130 may also be provided on the downstream side of the first dielectric layer 101.

The openings 110, 120, and 130 of the high-voltage electrode 100 described in FIGS. 5, 7 and 8 are different only in shape, but it is the same that the first conductive electrode layer 103 exposed to the outside through the openings 110, 120, and 130 emits ions. Alternatively, the high-voltage electrode 100 may include various shapes.

Figure 9:
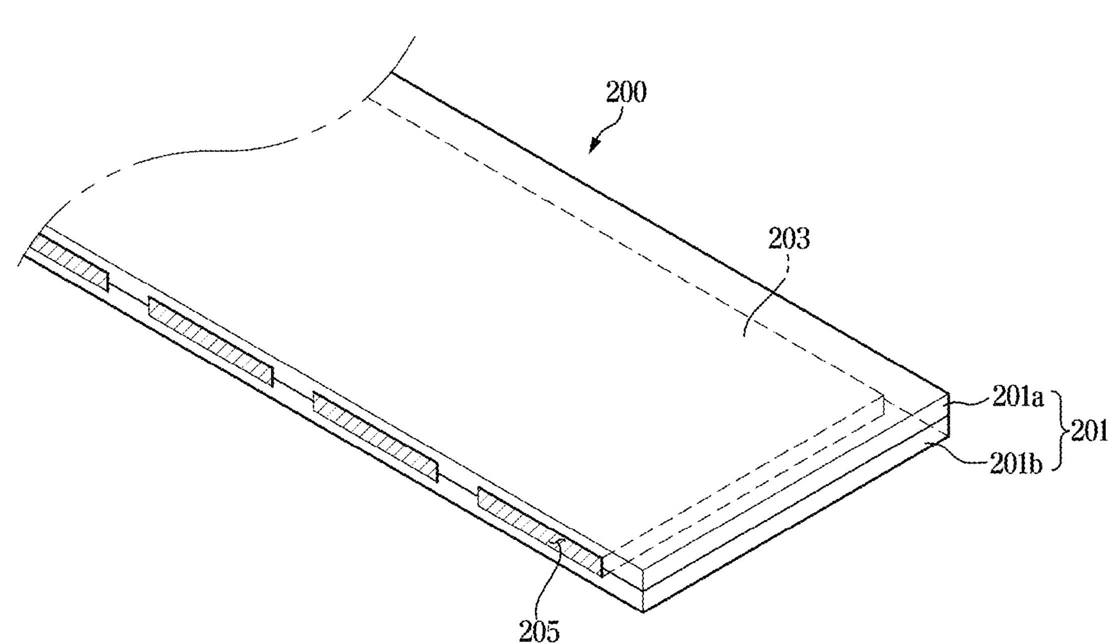
FIG. 9 is a view illustrating a low-voltage electrode according to a second embodiment.

FIG. 9 is a view illustrating a low-voltage electrode according to a second embodiment.

Referring to FIG. 9, a low-voltage electrode 200 of a dust collecting sheet 10 may include a plurality of openings 205. A plurality of straight-shaped openings 205 may also be formed on an upstream side of the low-voltage electrode 200. Alternatively, the opening 205 may also be provided on a downstream side of the low-voltage electrode 200. Based on the opening 205 formed in the low-voltage electrode 200, the charging effect on the aerosol may be increased. Although the openings 205 are illustrated as having a straight shape and being arranged at regular intervals, the disclosure is not limited thereto. The opening 205 may include a variety of shapes, and the position of the opening 205 may also vary.

Figure 10:
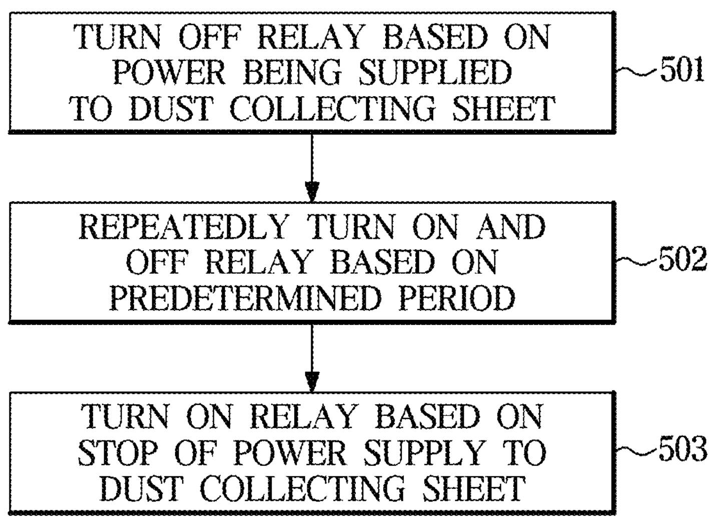
FIG. 10 is a flowchart illustrating a control method of the electrostatic precipitator according to an embodiment of the disclosure.

FIG. 10 is a flowchart illustrating a control method of the electrostatic precipitator according to an embodiment of the disclosure.

Referring FIG. 10, the controller 320 of the electrostatic precipitator 1 may control the power supplier 300 to supply power to the dust collecting sheet 10. In addition, the controller 320 may open (turn off) the relay 310 based on the supply of power to the dust collecting sheet 10 (501).

The controller 320 may control the relay 310 to be opened or closed based on the predetermined period (for example, 1 second). In other words, the controller 320 may control the relay 310 to be repeatedly turned on or off based on the predetermined period (502). The relay 310 may be turned on for a predetermined closing time (for example, 0.1 seconds) every predetermined period, and the relay 310 may be turned off for a predetermined opening time (for example, 0.9 seconds) every predetermined period.

The on/off period of the relay 310 may be designed differently depending on the characteristics of the electrostatic precipitator 1. For example, the on/off period of the relay 310 may be determined based on a rate at which the ion concentration measured at the front position of the electrostatic precipitator 1 changes. The ion concentration may be measured using a separate ion sensor (not shown) at the front position of the outside of the electrostatic precipitator 1. During a period of time in which the relay 310 is turned off after the start of the operation of the electrostatic precipitator 1, the concentration of ions measured in the front of the electrostatic precipitator 1 may be gradually reduced. This is because the potential difference between the filter assembly 3 and the high-voltage electrode 100 of the dust collecting sheet 10 is reduced. As the ion concentration is reduced rapidly, a single period of time for the on/off of the relay 310 may be determined to be shorter.

The controller 320 may set a time, for which the relay 310 is closed, to be less than a time, for which the relay 310 is opened. That is, the controller 320 may set the closing time of the relay 310 to be less than the opening time of the relay 310. For example, the controller 320 may set a ratio (duty ratio) of the closing time (ON time) of the relay 310 with respect to the predetermined period, to be less than or equal to 0.1.

As mentioned above, in response to an increase in the potential of the filter assembly 3 and in response to a reduction in the potential difference between the filter assembly 3 and the high-voltage electrode 100 in the opened state of the relay 310, the electric discharge may not be generated smoothly in the high-voltage electrode 100. In response to the relay 310 being closed, the ions accumulating in the filter assembly 3 may escape to the ground G and the potential difference between the filter assembly 3 and the high-voltage electrode 100 may be restored. For example, in response to the relative potential of the filter assembly 3 to the potential of the high-voltage electrode 100 being 1, the relay 310 may be closed.

After the potential difference between the filter assembly 3 and the high-voltage electrode 100 is restored by closing the relay 310 of the potential stabilizer, the relay 310 may be re-opened to allow the ions to be diffused through the filter assembly 3. By controlling the on/off of the relay 310 provided between the filter assembly 3 and the ground G, it is possible to effectively diffuse the ions emitted from the high-voltage electrode 100, and it is possible to increase the dust collecting efficiency of the electrostatic precipitator 1.

Meanwhile, the controller 320 may close (turn on) the relay 310 based on the stop of the power supply to the dust collecting sheet 10 (503). In response to the termination of the operation of the electrostatic precipitator 1, the supply of power to the dust collecting sheet 10 may be stopped. In response to the termination of the operation of the electrostatic precipitator 1, the controller 320 may turn on the relay 310 to allow the filter assembly 3 to be connected to the ground G. The relay 310 may be maintained in an on-state until the electrostatic precipitator 1 starts to operate again. In response to the termination of the operation of the electrostatic precipitator 1, an electric charge remaining in the filter assembly 3 may be removed to ensure the safety of the electrostatic precipitator 1.

FIGS. 11A, 11B, 11C and 11D are views illustrating an operation of the relay provided in the electrostatic precipitator according to an embodiment of the disclosure. FIG. 12 is a graph illustrating a relative potential and a relative ion concentration of the filter assembly that change according to an operation of the relay provided in the electrostatic precipitator according to an embodiment.

Referring to FIGS. 11A, 11B, 11C and 11D, the filter assembly 3 includes at least one of the filter mesh 40 or the grille 50. In addition, the filter assembly 3 may be formed of a conductive material. The graph of the relative potential of the filter assembly 3 in FIG. 12 shows that the relative potential of the filter assembly 3 with respect to the potential of the high-voltage electrode 100 changes with time. In addition, the ion concentration graph in FIG. 12 illustrates that the ion concentration emitted to the outside of the electrostatic precipitator 1 changes with time, and illustrates the relative ion concentration with respect to an initial ion concentration measured in response to the initial opening of the relay 310. The on/off period of the relay 310 is exemplified as 1 second. A starting point of X-axis of the graph in FIG. 12 is a starting point of the operation of the electrostatic precipitator 1.

Figure 11A:
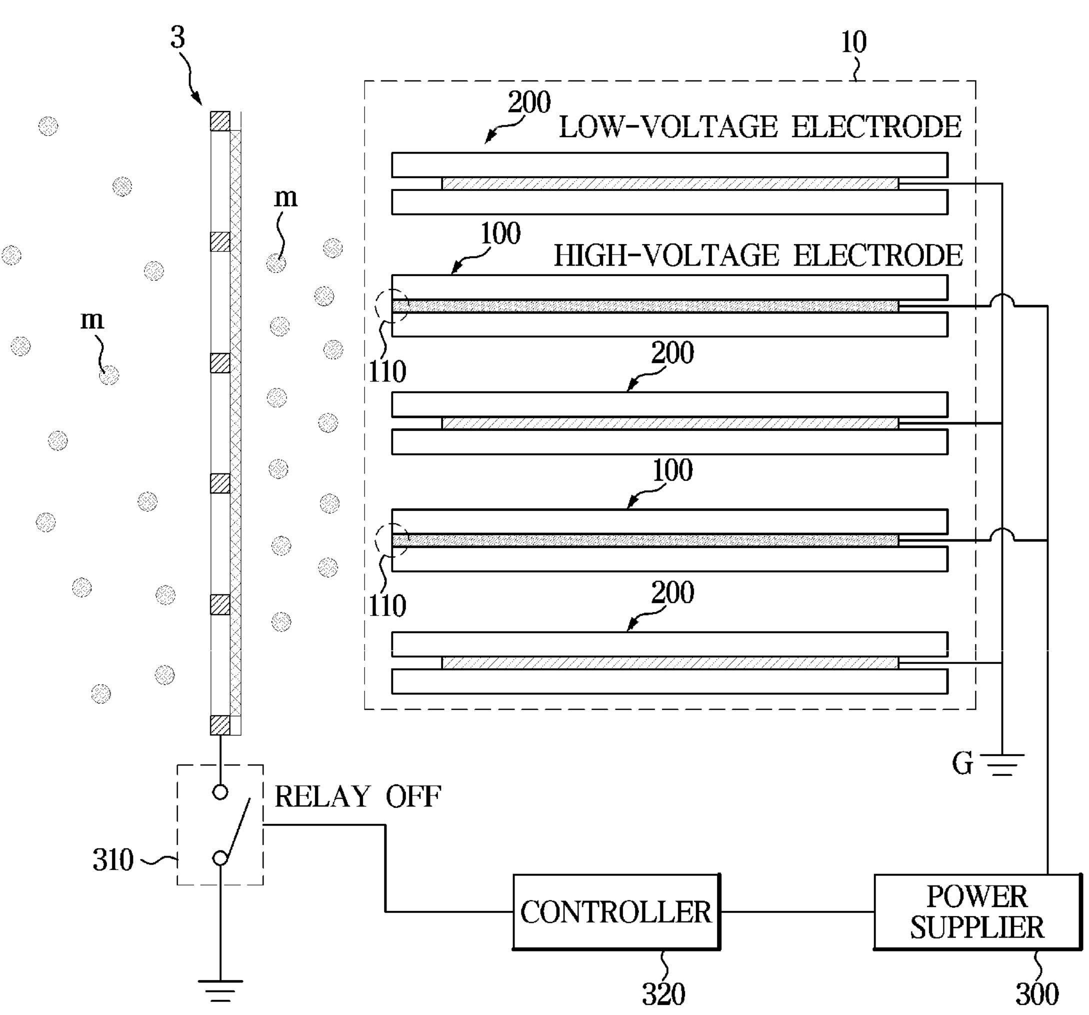
FIG. 11A is a view illustrating an operation of a relay provided in the electrostatic precipitator according to an embodiment of the disclosure.
Figure 12:
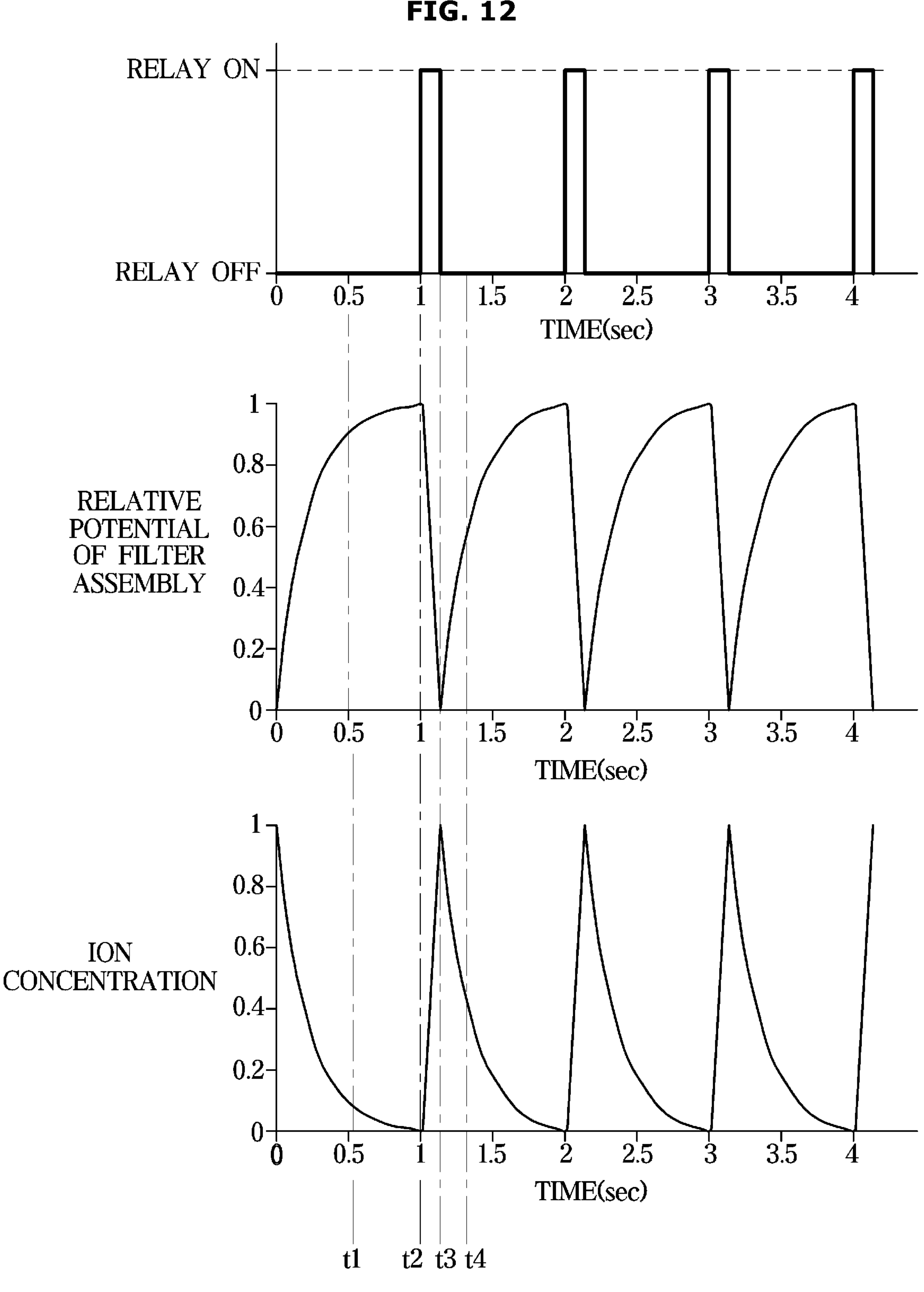
FIG. 12 is a graph illustrating a relative potential and a relative ion concentration of the filter assembly that change according to an operation of the relay provided in the electrostatic precipitator according to an embodiment.

Referring to FIG. 11A, in response to power being supplied to the dust collecting sheet 10, ions (m) are emitted from the high-voltage electrode 100 of the dust collecting sheet 10. In addition, in response to the relay 310 being opened (being turned off), some of the ions (m) emitted from the high-voltage electrode 100 are diffused into an external space located on the upstream side than the filter assembly 3, and another part of the ions (m) accumulate in the filter assembly 3.

Figure 11B:
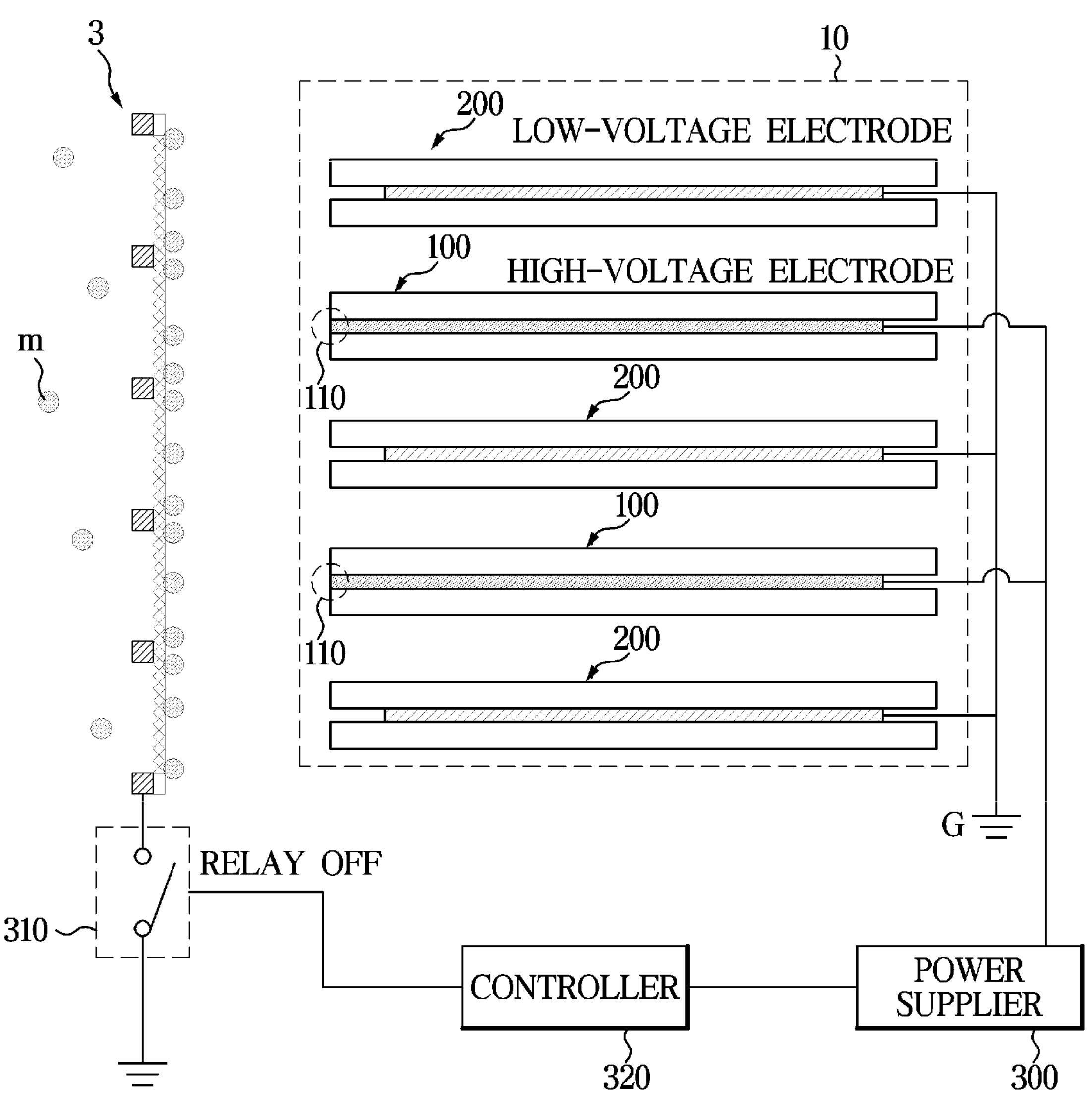
FIG. 11B is a view illustrating an operation of the relay provided in the electrostatic precipitator according to an embodiment of the disclosure.

Referring to FIG. 11B, during the relay 310 is opened, the amount of ions (m) accumulating in the filter assembly 3 is increased and the relative potential of the filter assembly 3 to the high-voltage electrode 100 is increased. In FIG. 12, it is seen that the relative potential of the filter assembly 3 is rapidly increased until a time t1 after the relay 310 is initially opened. It is seen that the concentration of ions (m) emitted to the front of the filter assembly 3 is rapidly reduced until the time t1 after the relay 310 is initially opened.

As the potential difference between the filter assembly 3 and the high-voltage electrode 100 is reduced, the discharge may not be generated smoothly in the high-voltage electrode 100, and the amount of ions (m) diffusing forward of the filter assembly 3 may be also reduced. Accordingly, the rate of increase in the relative potential of the filter assembly 3 observed between the time t 1 and a time t2, and the rate of decrease in the ion concentration measured at the front of the filter assembly 3 are reduced.

Figure 11C:
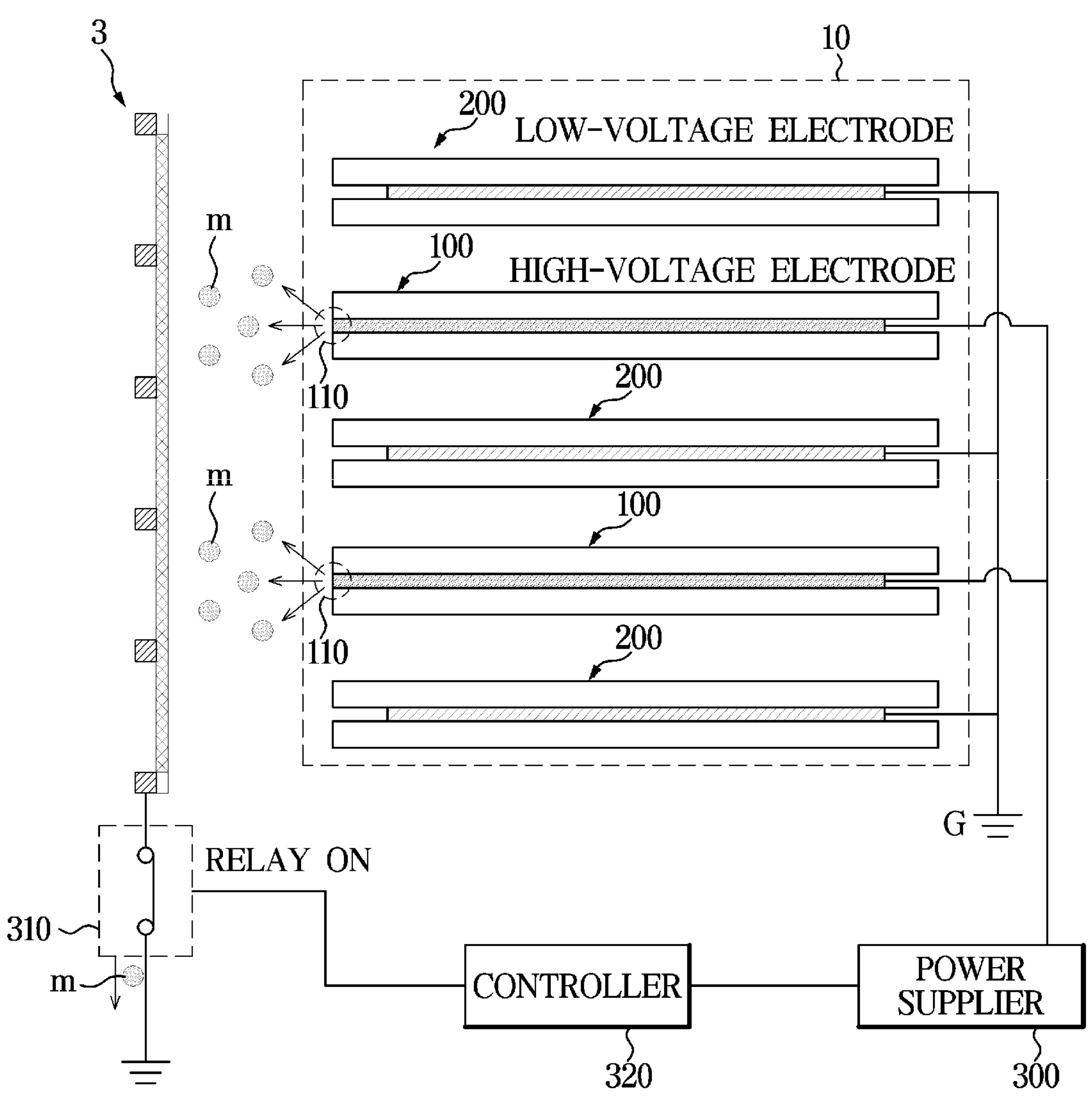
FIG. 11C is a view illustrating an operation of the relay provided in the electrostatic precipitator according to an embodiment of the disclosure.

Referring to FIG. 11C, in response to the relay 310 being closed, the ions (m) accumulating in the filter assembly 3 escape to the ground G. Accordingly, the potential difference between the filter assembly 3 and the high-voltage electrode 100 is restored. The electric discharge of the high-voltage electrode 100 is generated again smoothly, and the amount of ions (m) emitted from the high-voltage electrode 100 is increased.

Referring to FIG. 12, during from the time t2 to a time t3, the relay 310 is closed. That is, the relay 310 is turned on. Therefore, all ions (m) accumulating in the filter assembly 3 escape to the ground G during from the time t2 to the time t3. The relative potential of the filter assembly 3 is restored to 0 (zero), and the relative concentration of ions (m) emitted to the front of the filter assembly 3 is restored to 1.

Figure 11D:
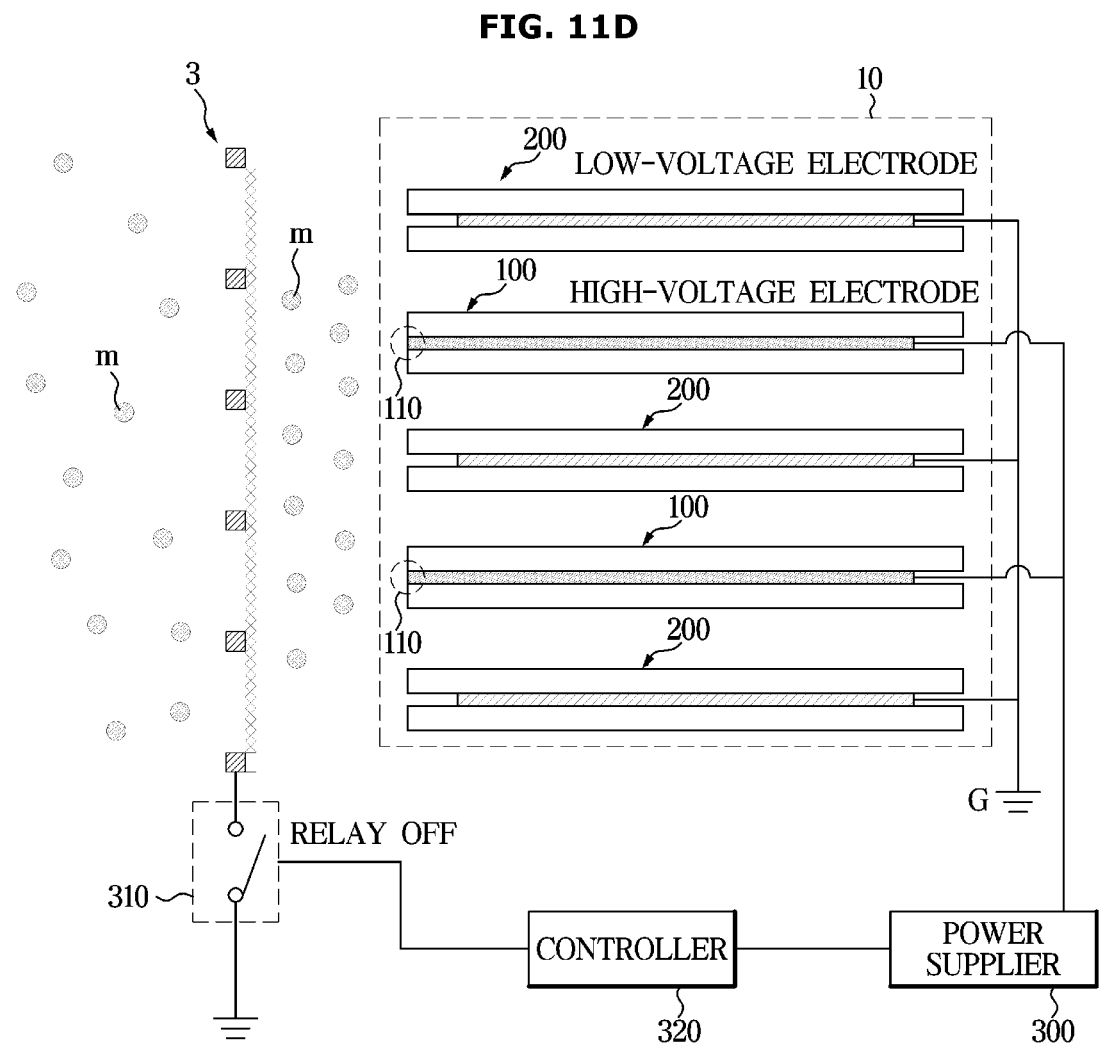

Referring to FIG. 11D, in response to the relay 310 being opened again, some of the ions (m) emitted from the high-voltage electrode 100 are diffused into an external space located on the upstream side of the filter assembly 3, and another part of the ions (m) accumulate in the filter assembly 3. In FIG. 12, it is seen that, in response to the relay 310 being opened again at the time t3, the relative potential of the filter assembly 3 is rapidly increased until a time t4, and the relative concentration of ions (m) emitted forward of the filter assembly 3 is reduced.

Figure 13:
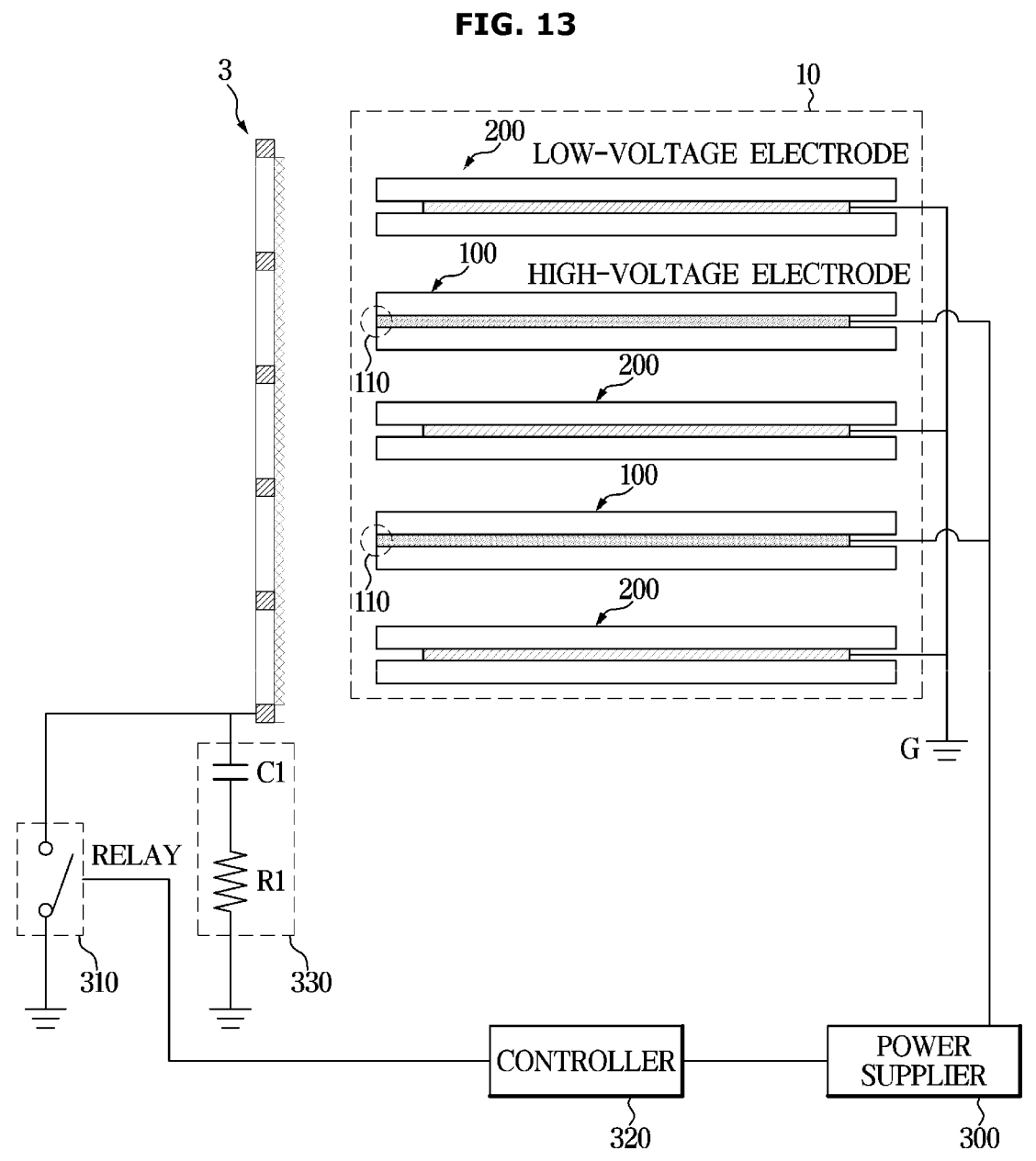
Figure 14:
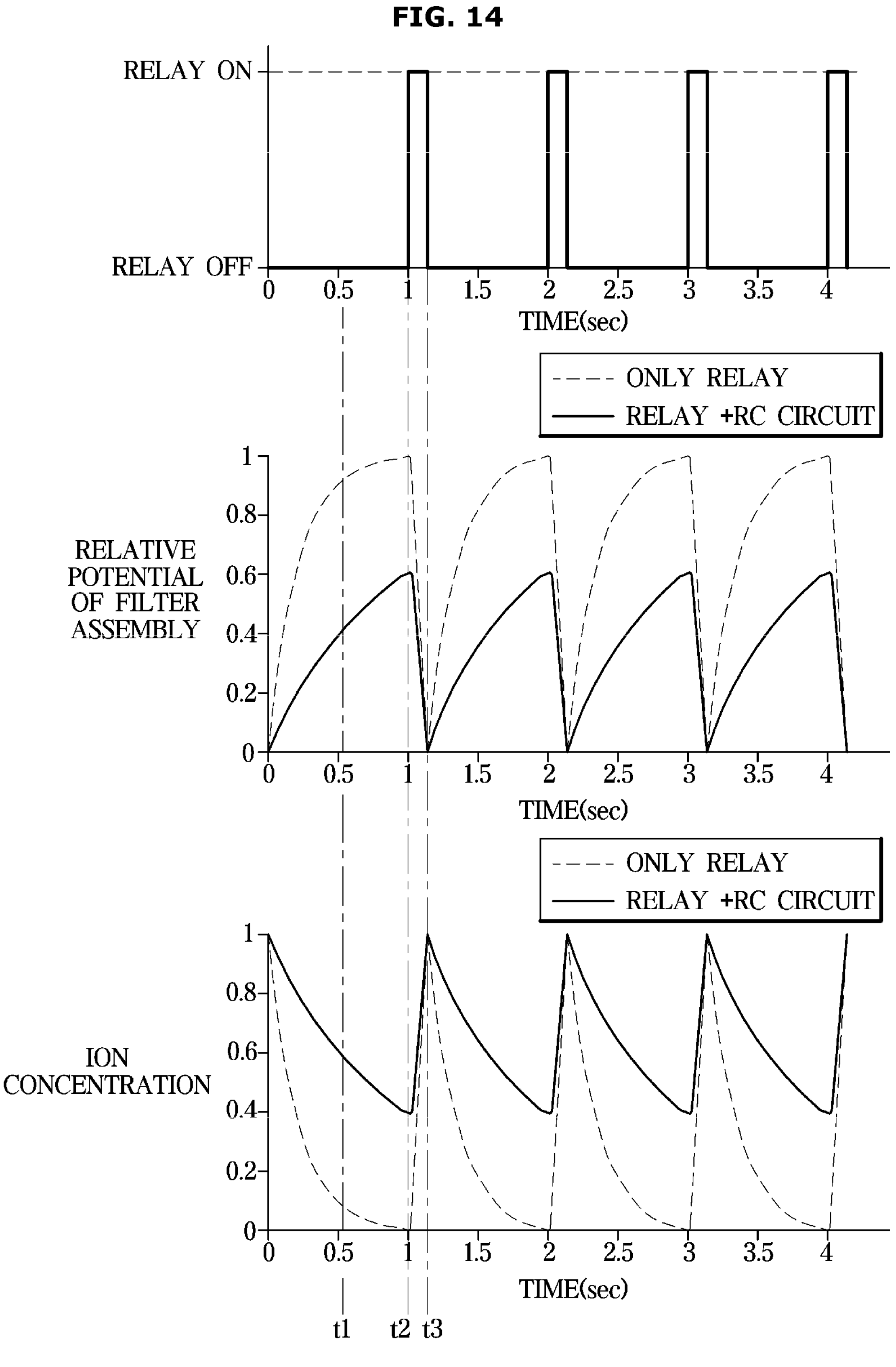
FIG. 14 is a graph illustrating a relative potential and a relative ion concentration of a filter assembly that change by an operation of a relay in the electrostatic precipitator including the RC circuit.

FIG. 13 is a view illustrating an additional embodiment of the electrostatic precipitator further including a resistor-capacitor (RC) circuit. FIG. 14 is a graph illustrating a relative potential and a relative ion concentration of a filter assembly that change by an operation of a relay in the electrostatic precipitator including the RC circuit.

Referring to FIG. 13, the electrostatic precipitator 1 may include a potential stabilizer arranged between the filter assembly 3 which is a plate-shaped structure and the ground G. As mentioned above, the potential stabilizer may include the relay 310 and may further include an RC circuit 330 connected in parallel with the relay 310. The RC circuit 330 may be arranged between the filter assembly 3 and the ground G. The RC circuit 330 may include a resistor R1 and a capacitor C1. The resistor R1 and the capacitor C1 may be connected in series.

In the state in which the relay 310 is opened, the RC circuit 330 may serve to reduce the rate at which ions accumulate in the filter assembly 3, and to reduce the relative potential of the filter assembly 3. The RC circuit 330 may prevent saturation of the ions (m) in the filter assembly 3. By the RC circuit 330, the potential of the filter assembly 3 may always be kept lower than the potential of the high-voltage electrode 100. Therefore, in a state in which both the relay 310 and the RC circuit 330 are provided, it is seen that the concentration of ions emitted to the front of the electrostatic precipitator 1 is relatively high.

Referring to FIG. 14, an embodiment, in which the electrostatic precipitator 1 includes the relay 310, is compared with the additional embodiment in which the electrostatic precipitator 1 includes both the relay 310 and the RC circuit 330. A change in a first relative potential of the filter assembly 3, and a change in a first relative ion concentration measured at the front of the filter assembly 3 in a state in which the RC circuit 330 is not provided, are indicated by dotted line graphs. A change in a second relative potential of the filter assembly 3, and a change in a second relative ion concentration measured at the front of the filter assembly 3 in a state in which the RC circuit 330 is provided, are indicated by solid line graphs In FIG. 14, it is seen that, in a state in which the RC circuit 330 is provided, a rate of increase of the relative potential of the filter assembly 3 and a rate of decrease of the ion concentration measured at the front of the filter assembly 3 after the relay 310 is opened are relatively reduced. In addition, it is seen that, by the RC circuit 330, the potential of the filter assembly 3 is always kept lower than the potential of the high-voltage electrode 100 and the concentration of ions emitted to the front of the electrostatic precipitator 1 is relatively high.

Figure 15:
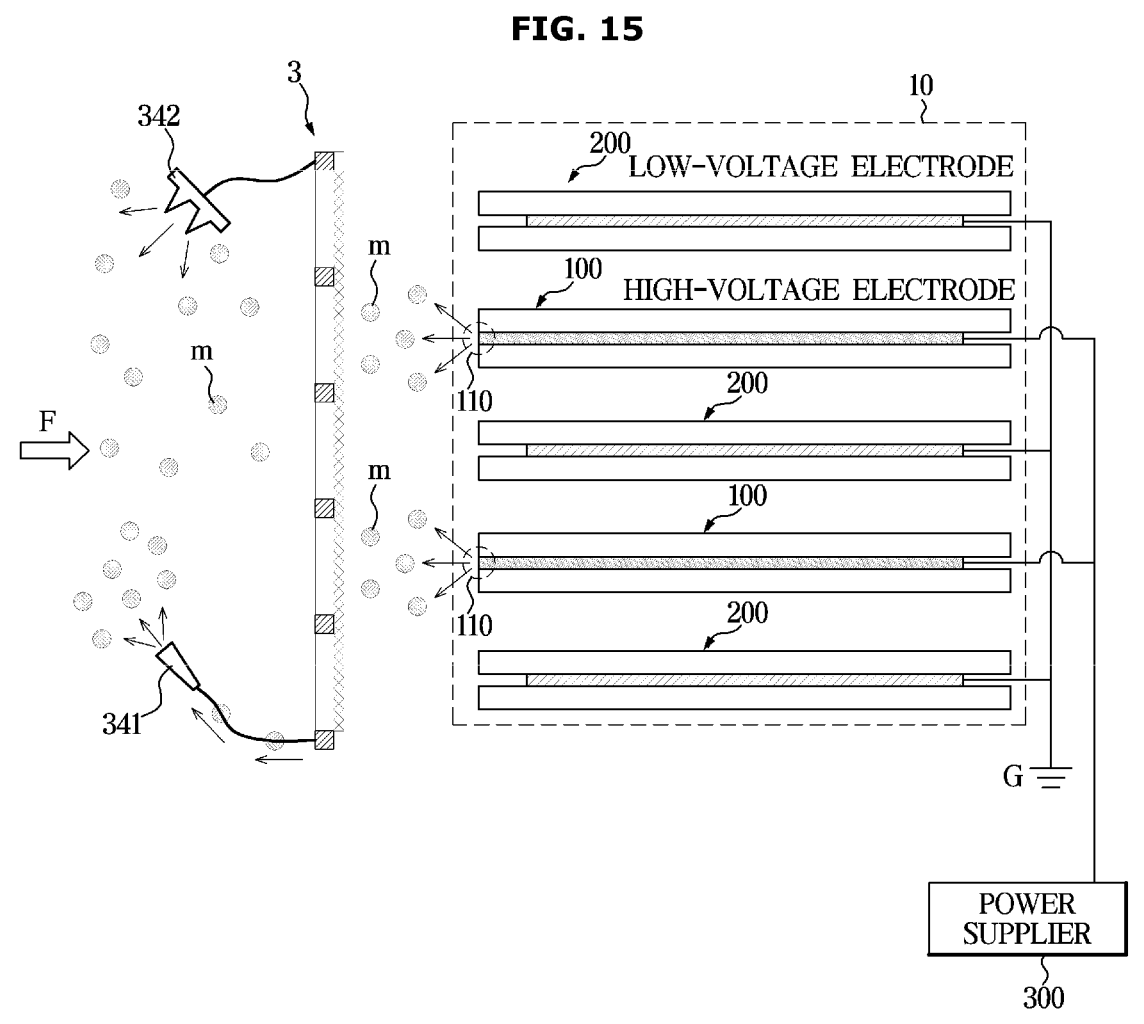

FIG. 15 is a view schematically illustrating an electrostatic precipitator including an ion emitter, according to another embodiment.

Referring to FIG. 15, an electrostatic precipitator 1 may include an ion emitter connected to the filter assembly 3 and configured to emit ions (m), which are moved from the high-voltage electrode 100 to the filter assembly 3, to the outside of the front of the electrostatic precipitator 1. The ions (m) may be moved along the surface of the filter assembly 3 composed of the filter mesh 40 and/or the grille 50 to the ion emitter, and then discharged to the outside through the ion emitter. Corona discharge may occur in a carbon brush 341 and a metal discharge pin 342, and thus the ions (m) may be emitted to the outside.

The ion emitter may be provided with at least one of the carbon brush 341 or the metal discharge pin 342. The carbon brush 341 and the metal discharge pin 342 have a relatively large of surface area to volume ratio. The metal discharge pin 342 may have various shapes. For example, the metal discharge pin 342 may be formed in a thumbtack shape. One or more ion emitters may be provided.

Meanwhile, based on the ion emitter being connected to the filter assembly 3, the relay 310 described above may be omitted. This is because the ions, which is provided to the filter assembly 3, are continuously emitted to the outside through the ion emitter. In addition, based on the ion emitter being connected to the filter assembly 3, the filter assembly 3 is not connected to the ground G.

Figure 16:
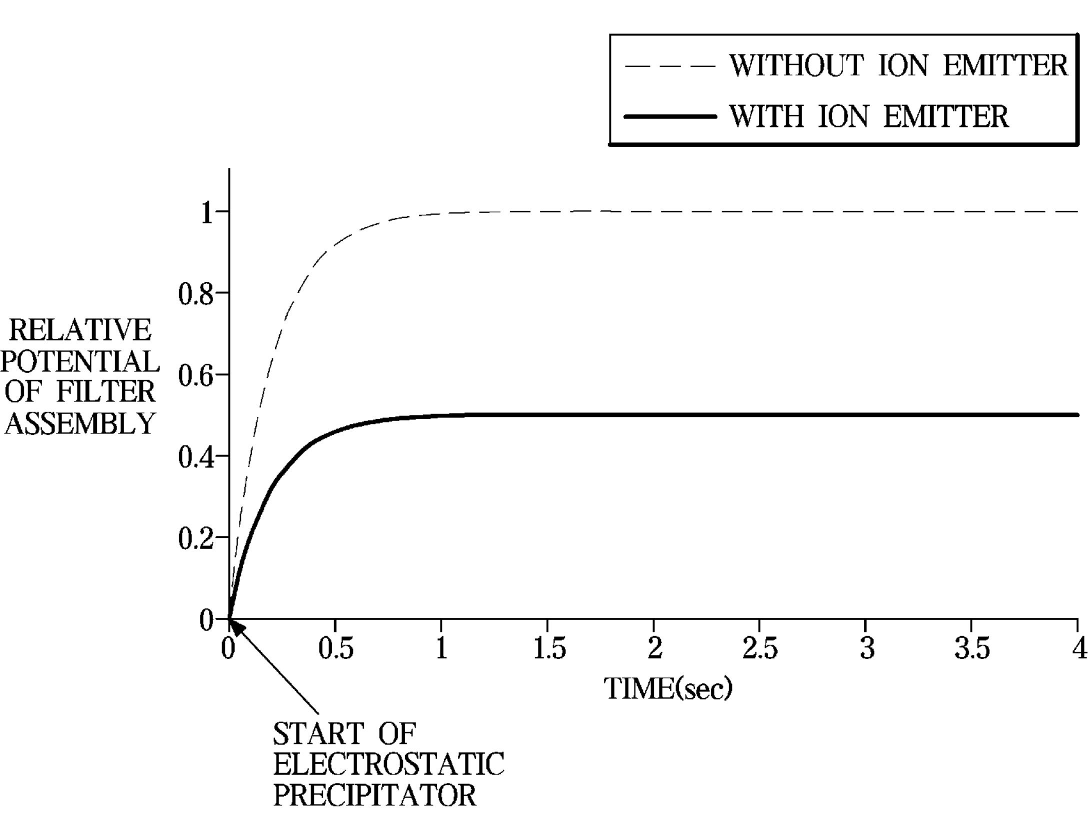
FIG. 16 is a graph illustrating a relative potential of a filter assembly during an operation of the electrostatic precipitator shown in FIG. 15.

FIG. 16 is a graph illustrating a relative potential of a filter assembly during an operation of the electrostatic precipitator shown in FIG. 15.

Referring to FIG. 16, an embodiment in which the ion emitter is connected to the filter assembly 3 is compared with another embodiment in which the ion emitter is not connected to the filter assembly 3. A change in the relative potential of the filter assembly 3 in the state, in which the ion emitter is not provided, is indicated by a dotted line graph. A change in the relative potential of the filter assembly 3 in the state, in which the ion emitter is provided, is indicated by a solid line graph.

In response to the filter assembly 3 including the filter mesh 40 and/or the grille 50, not being connected to the ground G and the ion emitter, ions accumulate on the surface of the filter assembly 3 according to the operation of the electrostatic precipitator 1. The ions accumulating in the filter assembly 3 may not be removed, and thus the potential of the filter assembly 3 becomes equal to the potential of the high-voltage electrode 100 over time. Accordingly, the electric discharge may not be generated in the high-voltage electrode 100.

In response to the filter assembly 3 being connected to the ion emitter, ions accumulate on the surface of the filter assembly 3, but the electric discharge is generated on the outside of the upstream side of the electrostatic precipitator 1 from the ion emitter. That is, the electric charges of the ions (m) are moved along the surface of the filter assembly 3 and escape to the outside through the ion emitter. Accordingly, the potential of the filter assembly 3 may be maintained to be lower than the potential of the high-voltage electrode 100, and the ions may be continuously emitted.

Figure 17:
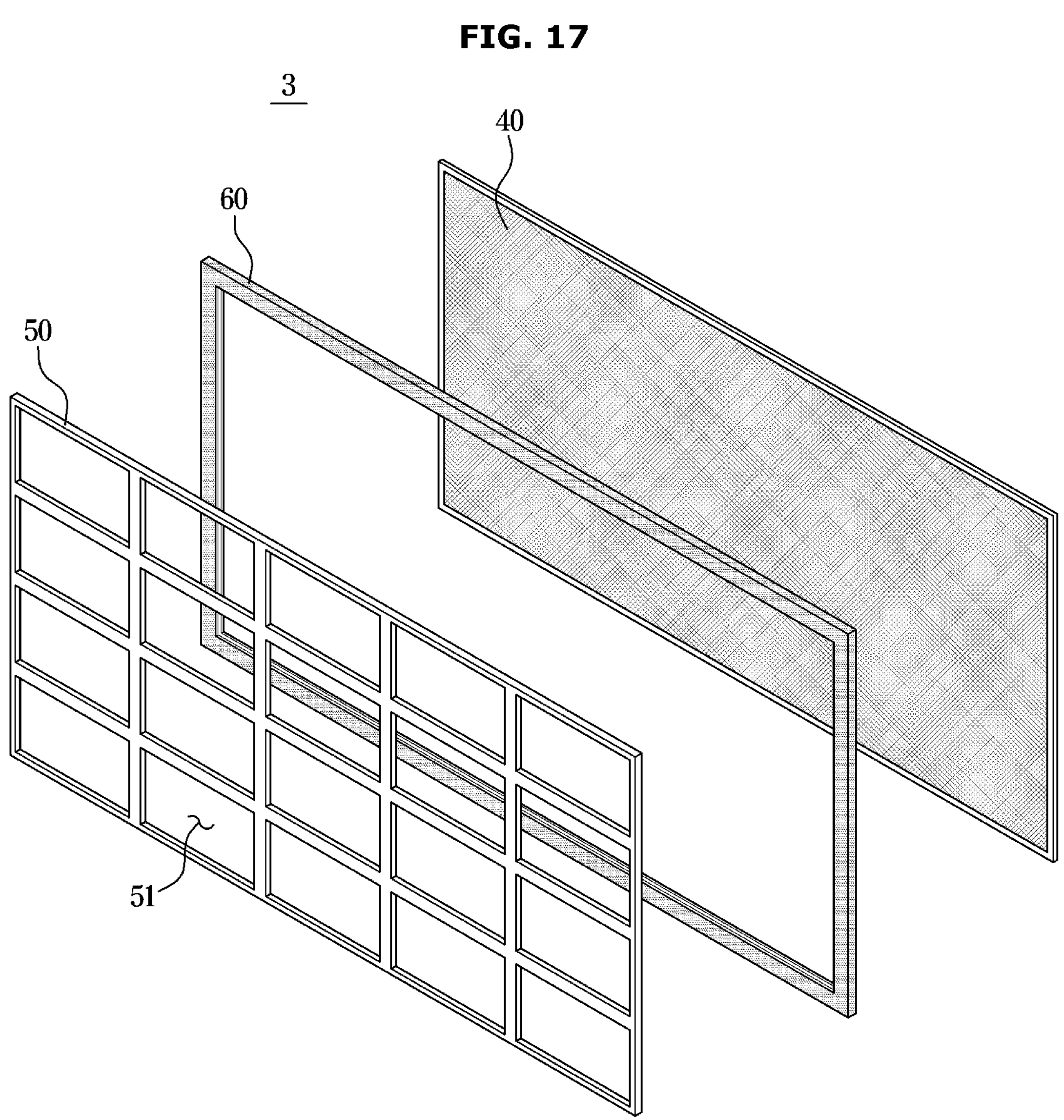
FIG. 17 is an exploded view illustrating a filter assembly according to another embodiment.
Figure 18:
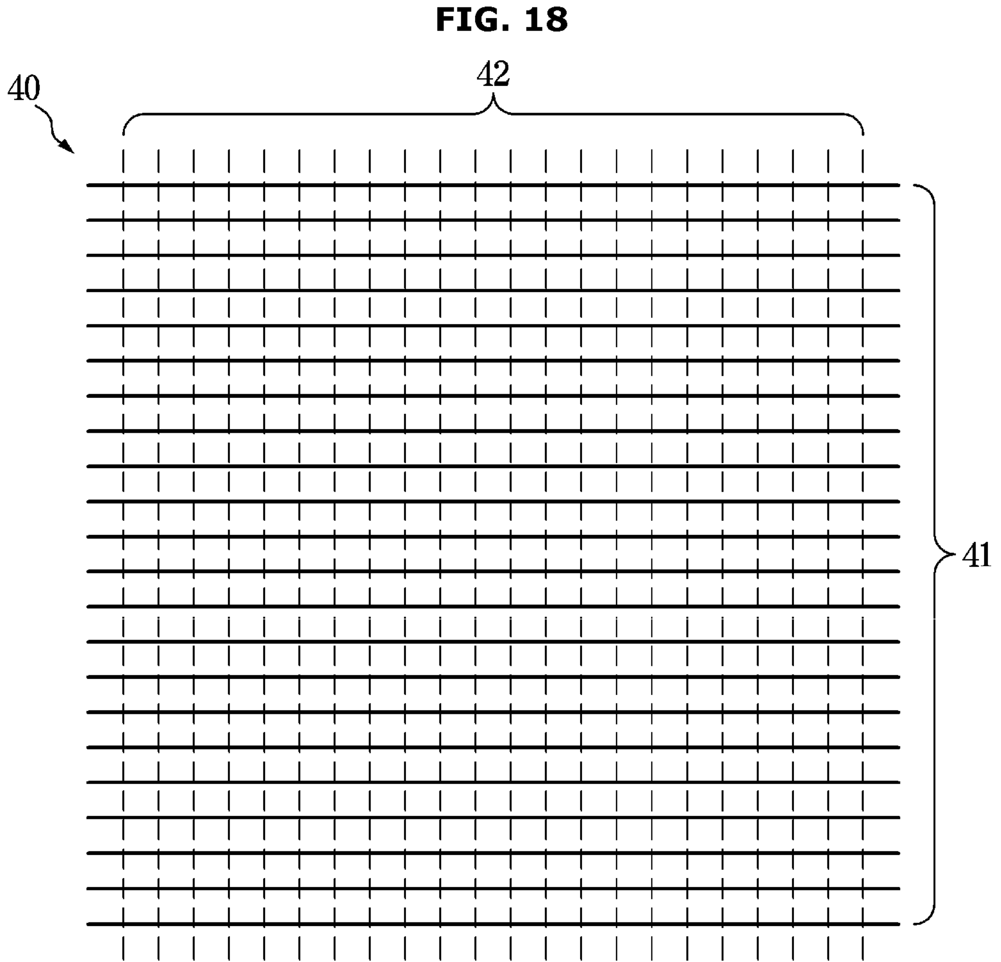
FIG. 18 is an enlarged view illustrating a part of a filter mesh included in the filter assembly.

FIG. 17 is an exploded view illustrating a filter assembly according to another embodiment. FIG. 18 is an enlarged view illustrating a part of a filter mesh included in the filter assembly.

As described in FIGS. 1 and 3, the filter assembly 3 may include the plate-shaped structure including at least one of the filter mesh 40 or the grille 50 including the plurality of openings. Referring to FIG. 17, the filter assembly 3 may further include a conductive member 60 provided on a rim of the plate-shaped structure.

For example, the filter mesh 40 and the grille 50 may be formed of a semi-conductive material having a uniform resistance as a whole. The plate-shaped structure may be referred to as a semi-conductive structure. A semi-conductive filter mesh 40 and a semi-conductive grille 50 may be integrally formed with each other or formed to be detachable from each other. The conductive member 60 may be referred to as an 'edge electrode'.

As another example, referring to FIG. 18, the filter mesh 40 may be formed of a combination of an insulator and a conductive material, or may be formed of a combination of an insulator and a semi-conductive material. That is, the filter mesh 40 may include a first member 41 formed of an insulator and a second member 42 formed of a conductive material or semi-conductive material. The first member 41 and the second member 42 may include a plurality of filaments. The first member 41 of the filter mesh 40 may include a plurality of filaments arranged transversely and formed of an insulator. The second member 42 of the filter mesh 40 may include a plurality of filaments arranged longitudinally and formed of a conductive material or a semi-conductive material. First filaments of the first member 41 and second filaments of the second member 42 may be arranged perpendicular to each other to form a lattice shape. The filaments corresponding to the first member 41 are indicated by a solid line, and the filaments corresponding to the second member 42 are indicated by a dashed line.

The filter assembly 3 may be formed in a plate shape. The filter assembly 3 may include a shape corresponding to the shape of the dust collection assembly 2 (for example, quadrangle or circle). That is, the plate-shaped structure may have various shapes (for example, quadrangle or circle). The filter assembly 3 may be arranged at a position spaced apart from the dust collecting sheet 10 by a predetermined distance. It may be appropriate that the filter assembly 3 is spaced apart from the dust collecting sheet 10 by a distance within a range of greater than or equal to 4 mm, but less than or equal to 10 mm.

FIG. 17 illustrates an embodiment in which the conductive member 60 is provided on the rim of the plate-shaped structure in which the filter mesh 40 and the grille 50 are integrally formed with each other. However, the filter mesh 40 or the grille 50 may be exclusively provided, and the conductive member 60 may be provided on each rim of the filter mesh 40 and the grille 50.

The conductive member 60 may be provided on at least one portion of the rim of the plate-shaped structure. FIG. 17 illustrates that the conductive member 60 is provided to cover the entire rim of the plate-shaped structure, but the conductive member 60 may be provided on a portion of the rim of the plate-shaped structure, as described below.

Based on the filter assembly 3 being placed perpendicular to the ground surface, the grille 50 may be provided at the front or rear of the filter mesh 40. The grille 50 may be integrally formed with the filter mesh 40 or coupled to the filter mesh 40. The grille 50 may protrude from the surface of the filter mesh 40. The grille 50 may include the plurality of openings 51. The grille 50 may support the filter mesh 40 and protect the filter mesh 40.

Figure 19:
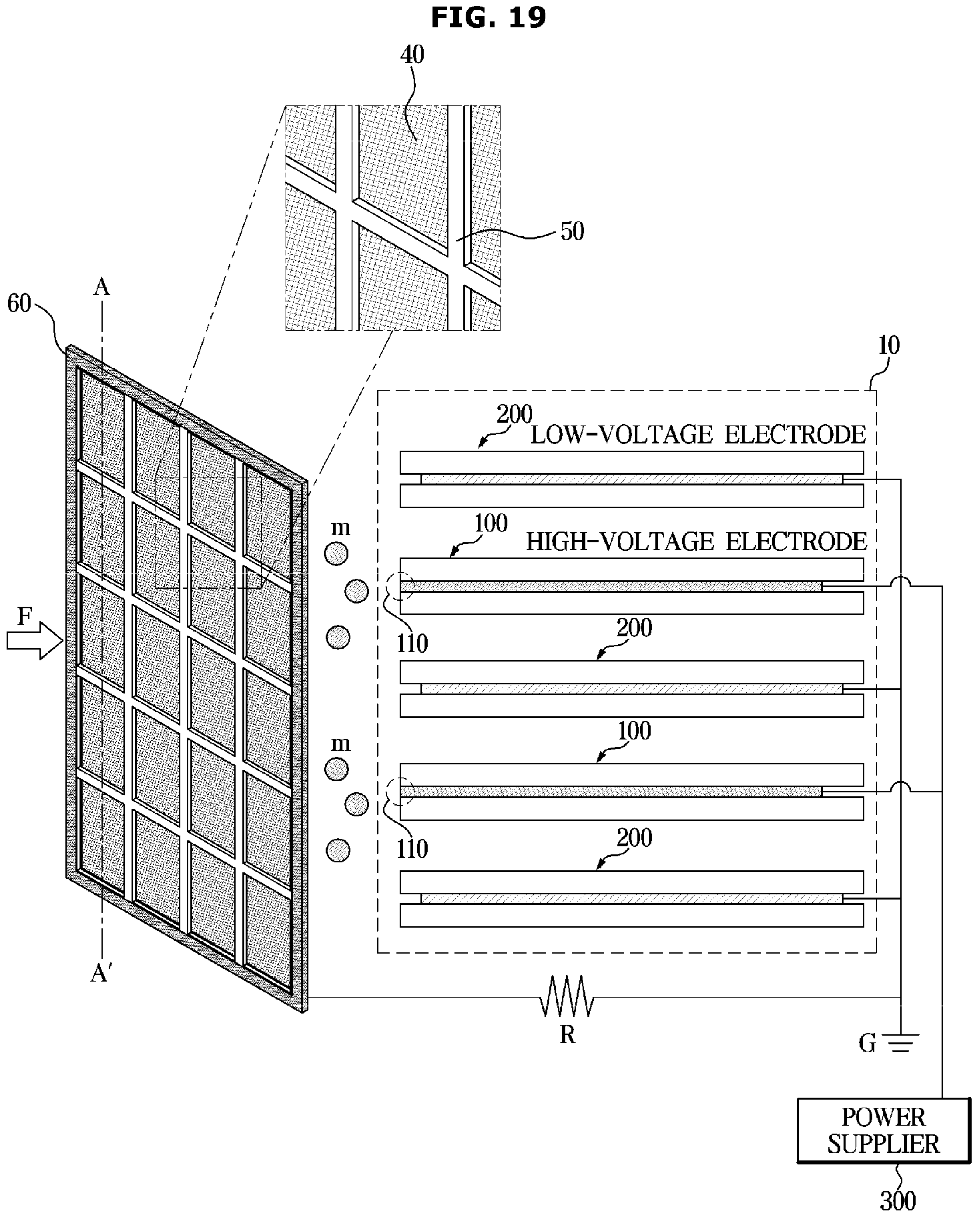
FIG. 19 is a view schematically illustrating configurations of the electrostatic precipitator shown in FIG. 17.

FIG. 19 is a view schematically illustrating configurations of the electrostatic precipitator shown in FIG. 17.

As mentioned above, based on the entire filter assembly 3 being formed of a non-conductive material, the non-conductive material has dielectric properties and thus dielectric polarization may occur in the filter assembly 3. In this case, ions accumulate in the filter assembly 3 and the filter assembly 3 has a potential. Therefore, the potential difference between the high-voltage electrode 100 and the filter assembly 3 of the dust collecting sheet 10 is reduced, and thus the amount of charge of the aerosol flowing into the dust collecting sheet 10 is reduced, thereby reducing the collection efficiency of the aerosol.

Based on the filter assembly 3 being formed of a conductive material and the filter assembly 3 being connected to the ground G, ions emitted from the high-voltage electrode 100 of the dust collecting sheet 10 may quickly escape to the ground through the filter assembly 3. A surface resistance of the conductive material may be less than $10^6$ [ohm/sq]. Therefore, the ions may not be diffused into space, and the amount of charge of the aerosol in the air flowing into the dust collecting sheet 10 is reduced, thereby reducing the collection efficiency of the aerosol. In addition, sparks may be generated in response to the filter assembly 3 formed of a conductive material, being arranged adjacent to the high-voltage electrode 100.

Based on the filter assembly 3 being formed of a semi-conductive material, among the surface region of the filter assembly 3, a non-uniform electric field may be formed between a region close to the ground G and a region far from the ground G. In this case, more ions emitted from the high-voltage electrode 100 may be collected in a partial region of the filter assembly 3. Accordingly, the amount of charge of the aerosol in the air flowing into the dust collecting sheet 10 may be reduced, and the collection efficiency of the aerosol may be reduced.

To ease the difficulty, the filter assembly 3 of the disclosed electrostatic precipitator 1 may include a conductive member 60 provided on the rim of the plate-shaped structure. The plate-shaped structure may include at least one of the filter mesh 40 or the grille 50. For example, the filter mesh 40 and the grille 50 formed of a semi-conductive material may have a surface resistance of greater than or equal to $10^6$ [ohm/sq], but less than or equal to $10^{11}$ [ohm/sq]. However, the surface resistance is not limited thereto, and thus the filter mesh 40 and the grille 50 may have a different surface resistance depending on the discharge characteristics.

The conductive member 60 of the filter assembly 3 may form an electric field in the plate-shaped structures 40 and 50 so as to diffuse the ions (m) emitted from the high-voltage electrode 100 of the dust collecting sheet 10. The conductive member 60 may be provided on the rim of the plate-shaped structures 40 and 50 to form a uniform electric field in the plate-shaped structures 40 and 50. The ions (m) emitted from the high-voltage electrode 100 may be evenly distributed over the entire region of the plate-shaped structures 40 and 50. Accordingly, the dust collection efficiency may be increased.

The conductive member 60 may be connected to the ground G. A resistance element R may be provided between the conductive member 60 and the ground G. The resistance element R may prevent excessive current from flowing through the semiconductive structures 40 and 50. For example, the resistance element R may be greater than or equal to $10^6$ [ohm], but less than or equal to $10^{11}$ [ohm]. However, the resistance element R is not limited thereto, and thus resistance element R may have a different resistance value depending on the discharge characteristics. Even if the filter assembly 3 is arranged close to the dust collecting sheet 10, the resistance element R may prevent the generation of the sparks and discharge noise. The resistance element R may be referred to as a 'potential stabilizer' for stabilizing the potential of the filter assembly 3.

Although not shown in FIG. 19, a relay 310 may be further provided between the conductive member 60 and the ground G or between the conductive member 60 and the resistor R. As illustrated in FIG. 4, in response to the relay 310 being opened, the filter assembly 3 is not connected to the ground G. Therefore, the ions (m) may be evenly distributed in the surface region of the filter mesh 40 and the grille 50 formed of a semi-conductive material, and the ions (m) may be diffused from the entire surface region of the filter assembly 3 to the external space on the upstream side. That is, by connecting the relay 310 to the filter assembly 3, and by controlling the on/off the relay 310, it is possible to further increase the diffusion of ions (m) and dust collection efficiency of the electrostatic precipitator 1.

Figure 20:
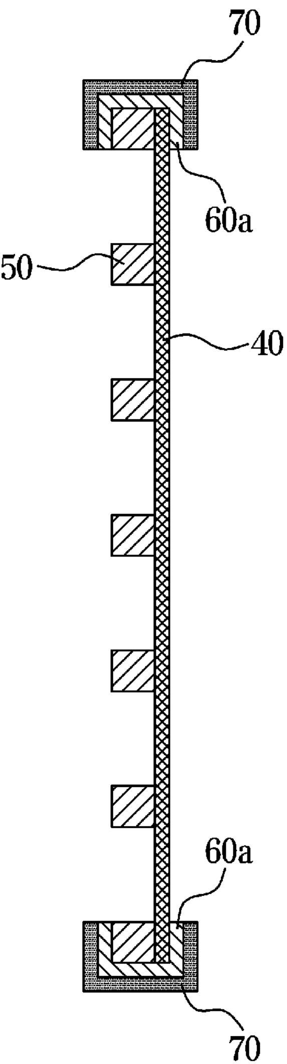
FIG. 20 is a view illustrating a first type of a conductive member provided in the filter assembly.

FIG. 20 is a view illustrating a first type of a conductive member provided in the filter assembly.

FIG. 20 is a cross-sectional view taken along line A-A' of the quadrangular plate-shaped structures 40 and 50 of FIG. 19. A conductive member 60*a* according to an embodiment may be provided on the rim of the plate-shaped structures 40 and 50. For example, the conductive member 60*a* may include a bent shape to surround the rim of the plate-shaped structures 40 and 50. A cross-section of the conductive member 60*a* may include a shape of square brackets.

Because the cross-section of the conductive member 60*a* includes the bent shape, that is, the square bracket shape, it is possible to surround the rim of the plate-shaped structures 40 and 50 composed of the filter mesh 40 and the grille 50. In response to the conductive member 60*a* being charged by ions or receiving a voltage, an electric field may be uniformly formed in the entire region of the plate-shaped structures 40 and 50.

As another example, the conductive member 60 may include a bar shape having a quadrangular cross-section, and be attached to a side surface of the plate-shaped structure 40 and 50. In addition, the conductive member 60 may be provided in various shapes on the rim of the plate-shaped structures 40 and 50.

The filter mesh 40 and the grille 50 may be integrally formed with each other. In addition, the filter mesh 40 and the grille 50 may be detachably coupled to each other. The grille 50 may protrude from the surface of the filter mesh 40. The grille 50 may support the filter mesh 40 and protect the filter mesh 40.

The conductive member 60 may be formed integrally with the plate-shaped structures 40 and 50, or may be provided detachably from the plate-shaped structures 40 and 50. In addition, an insulating member 70 may be provided outside the conductive member 60*a* to cover the conductive member 60*a*. The insulating member 70 may be coated on the conductive member 60*a*. By providing the insulating member 70, it is possible to more effectively prevent the generation of sparks between the dust collection assembly 2 and the filter assembly 3 and further reduce a distance between the plate-shaped structures 40 and 50 and the dust collecting sheet 10.

Figure 21:
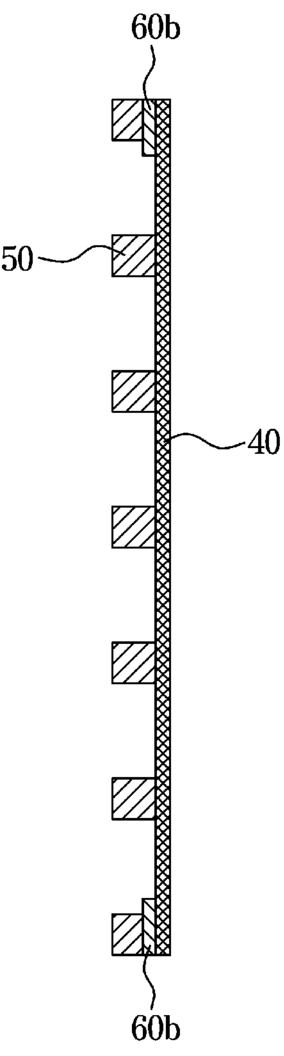
FIG. 21 is a view illustrating a second type of the conductive member provided in the filter assembly.

FIG. 21 is a view illustrating a second type of the conductive member provided in the filter assembly.

Referring to FIG. 21, a conductive member 60*b* may be arranged between the filter mesh 40 and the grille 50. The conductive member 60*b* may be attached to the surfaces of the plate-shaped structures 40 and 50. For example, the conductive member 60*b* may be provided so as to be in contact with a corner where a wide surface and a side surface of the filter mesh 40 meet. In addition, the conductive member 60*b* may be provided to be in contact with an edge surface of the grille 50.

The conductive member 60*b* may include a quadrangular cross-section, and may be provided to have a line shape along the edges of the plate-shaped structures 40 and 50. Based on the plate-shaped structures 40 and 50 including a quadrangular plate shape, the conductive member 60*b* may be attached to the surface of the plate-shaped structures 40 and 50 so as to have a bar shape along the corner of the plate-shaped structures 40 and 50.

In addition, the insulating member 70 described in FIG. 20 may also be applied to the embodiment of FIG. 21. The insulating member 70 may be provided to surround the conductive member 60*b* arranged between the semi-conductive filter mesh 40 and the semi-conductive grille 50. That is, the insulating member 70 may be provided to cover edges of the plate-shaped structures 40 and 50.

Figure 22:
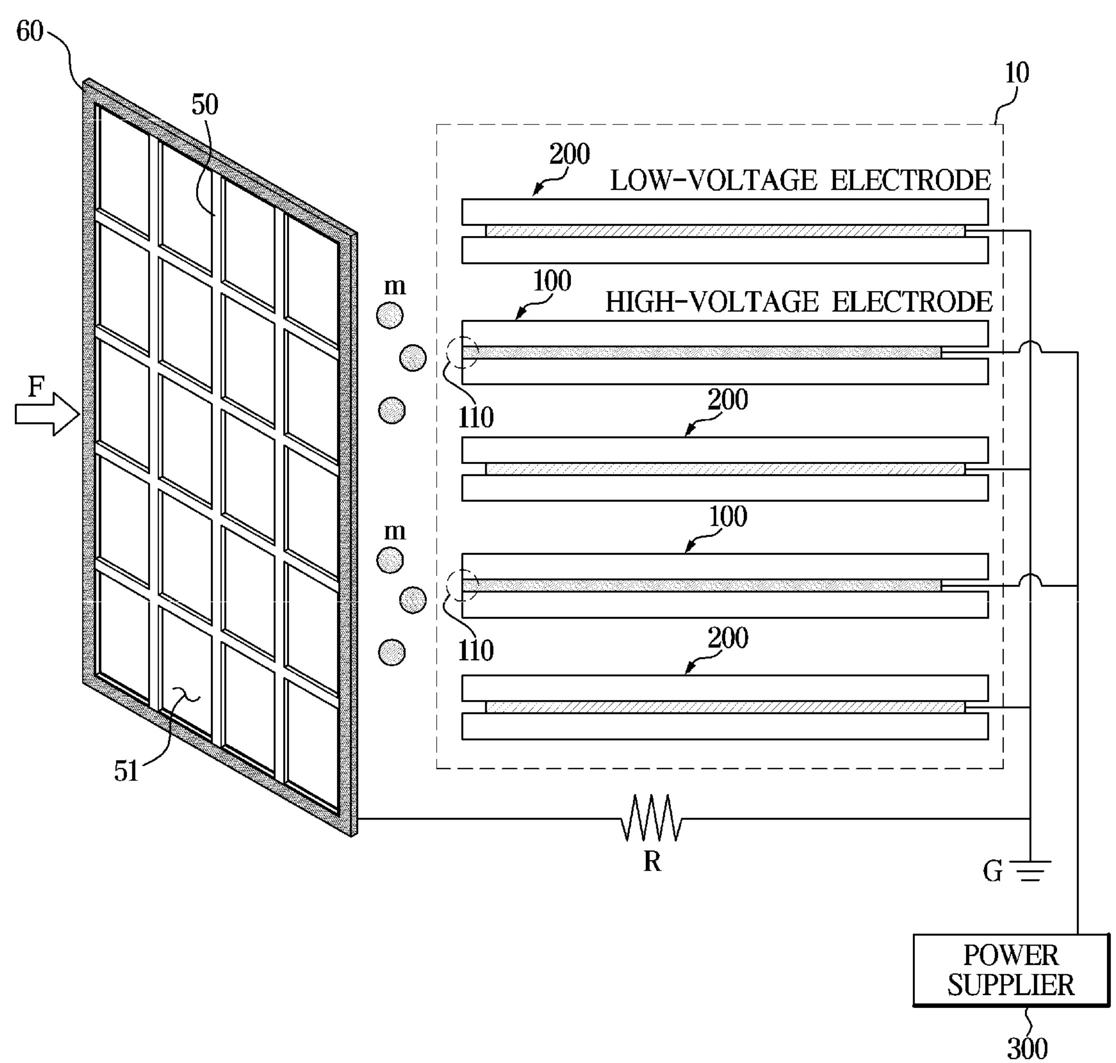
FIG. 22 is a view illustrating an example in which a conductive member is provided on a rim of a grille.

FIG. 22 is a view illustrating an example in which a conductive member is provided on a rim of a grille.

Referring to FIG. 22, the filter assembly 3 may include only a grille 50. As mentioned above, the grille 50 may be formed of a semi-conductive material. The semi-conductive grille 50 may include a plate shape and may include a plurality of openings 51. The openings 51 of the semi-conductive grille 50 may prevent a material having a size greater than a size of one opening 51 from flowing into the dust collecting sheet 10.

A conductive member 60 may be provided on a rim of the semi-conductive grille 50. The conductive member 60 may be provided on at least one portion of the rim of the semi-conductive grille 50. For example, the conductive member 60 may be provided to cover the entire rim of the semi-conductive grille 50. The conductive member 60 may be provided on a part of the rim of the semi-conductive grille 50.

Air may pass through the semi-conductive grille 50 and the dust collecting sheet 10 along the direction F. The dust collecting sheet 10 may emit ions (m) to positively (+) or negatively (−) charge the aerosol in the air. The air may be charged before reaching the dust collecting sheet 10. Air may be charged while passing through the semi-conductive grille 50. The charged air may pass between the high-voltage electrode 100 and the low-voltage electrode 200.

By arranging the conductive member 60 on the rim of the semi-conductive grille 50, a uniform electric field may be formed over the entire region of the semi-conductive grille 50. Accordingly, the ions (m) emitted from the dust collecting sheet 10 may be evenly spread over the entire region of the semi-conductive grille 50.

The conductive member 60 may be connected to the ground G. A resistance element R may be provided between the conductive member 60 and the ground G.

The resistance element R may prevent excessive current from flowing through the plate-shaped structures 40 and 50. For example, the resistance element R may be greater than or equal to $10^6$ [ohm], but less than or equal to $10^{11}$ [ohm]. However, the resistance element R is not limited thereto, and thus resistance element R may have a different resistance value depending on the discharge characteristics. Even if the semi-conductive grille 50 is arranged close to the dust collecting sheet 10, the resistance element R may prevent the generation of the sparks and discharge noise.

In a state in which the plate-shaped structures 40 and 50 are arranged at a position sufficiently far from the dust collecting sheet 10, the spark may not be generated between the plate-shaped structures 40 and 50 and the dust collecting sheet 10, and thus the resistance element R between the conductive member 60 and the ground G may be omitted.

In addition, the insulating member 70 described in FIG. 20 may be provided outside the conductive member 60 to cover the conductive member 60.

Figure 23:
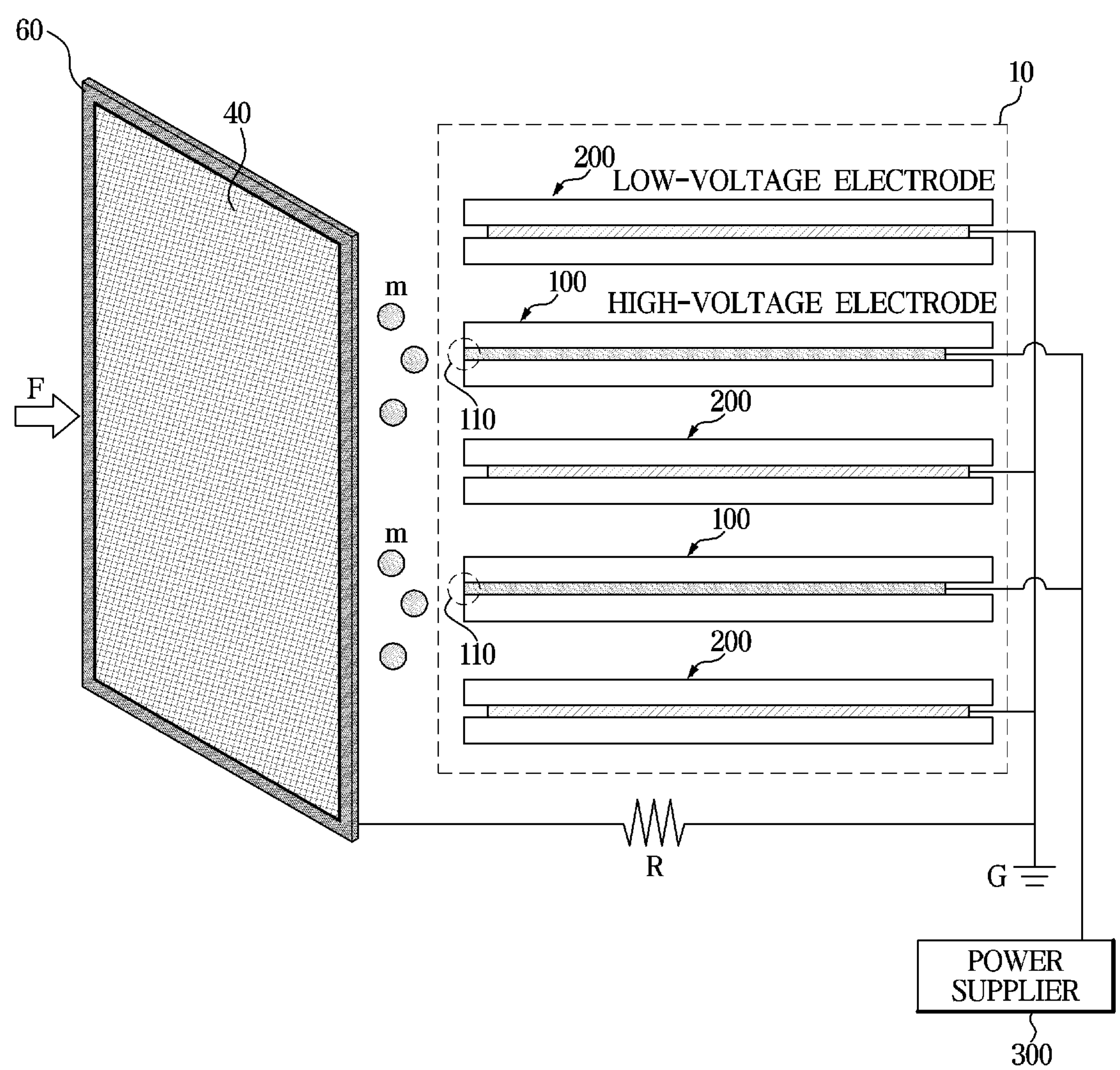
FIG. 23 is a view illustrating an example in which the conductive member is provided on a rim of a filter mesh.

FIG. 23 is a view illustrating an example in which the conductive member is provided on a rim of a filter mesh.

Referring to FIG. 23, the filter assembly 3 may include only a filter mesh 40. As mentioned above, the filter mesh 40 may include a plate shape and may include a plurality of micro-holes. The filter mesh 40 may prevent a material having a size greater than a predetermined size from flowing into the dust collecting sheet 10. The filter mesh 40 may be formed of a semi-conductive material having a uniform resistance as a whole, or formed of a combination of an insulator and a conductive material, or formed of a combination of an insulator and a semi-conductive material.

A conductive member 60 may be provided on a rim of the filter mesh 40. The conductive member 60 may be provided on at least one portion of the rim of the filter mesh 40. For example, the conductive member 60 may be provided to cover the entire rim of the filter mesh 40. The conductive member 60 may be provided on a part of the rim of the filter mesh 40. The conductive member 60 may serve as a support for supporting the filter mesh 40.

Air may pass through the filter mesh 40 and the dust collecting sheet 10 along the direction F. The dust collecting sheet 10 may emit ions (m) to positively (+) or negatively (−) charge the aerosol in the air. The air may be charged before reaching the dust collecting sheet 10. Air may be charged while passing through the filter mesh 40. The charged air may pass between the high-voltage electrode 100 and the low-voltage electrode 200.

By arranging the conductive member 60 on the rim of the filter mesh 40, a uniform electric field may be formed over the entire region of the filter mesh 40. Accordingly, the ions (m) emitted from the dust collecting sheet 10 may be evenly spread over the entire region of the filter mesh 40.

The conductive member 60 may be connected to the ground G. FIG. 23 illustrates an embodiment in which the resistance element R is omitted between the conductive member 60 and the ground G. In response to the filter 40 is arranged at a position sufficiently far from the dust collecting sheet 10, the spark may not be generated between the filter mesh 40 and the dust collecting sheet 10 and thus the resistance element R between the conductive member 60 and the ground G may be omitted.

Figure 24:
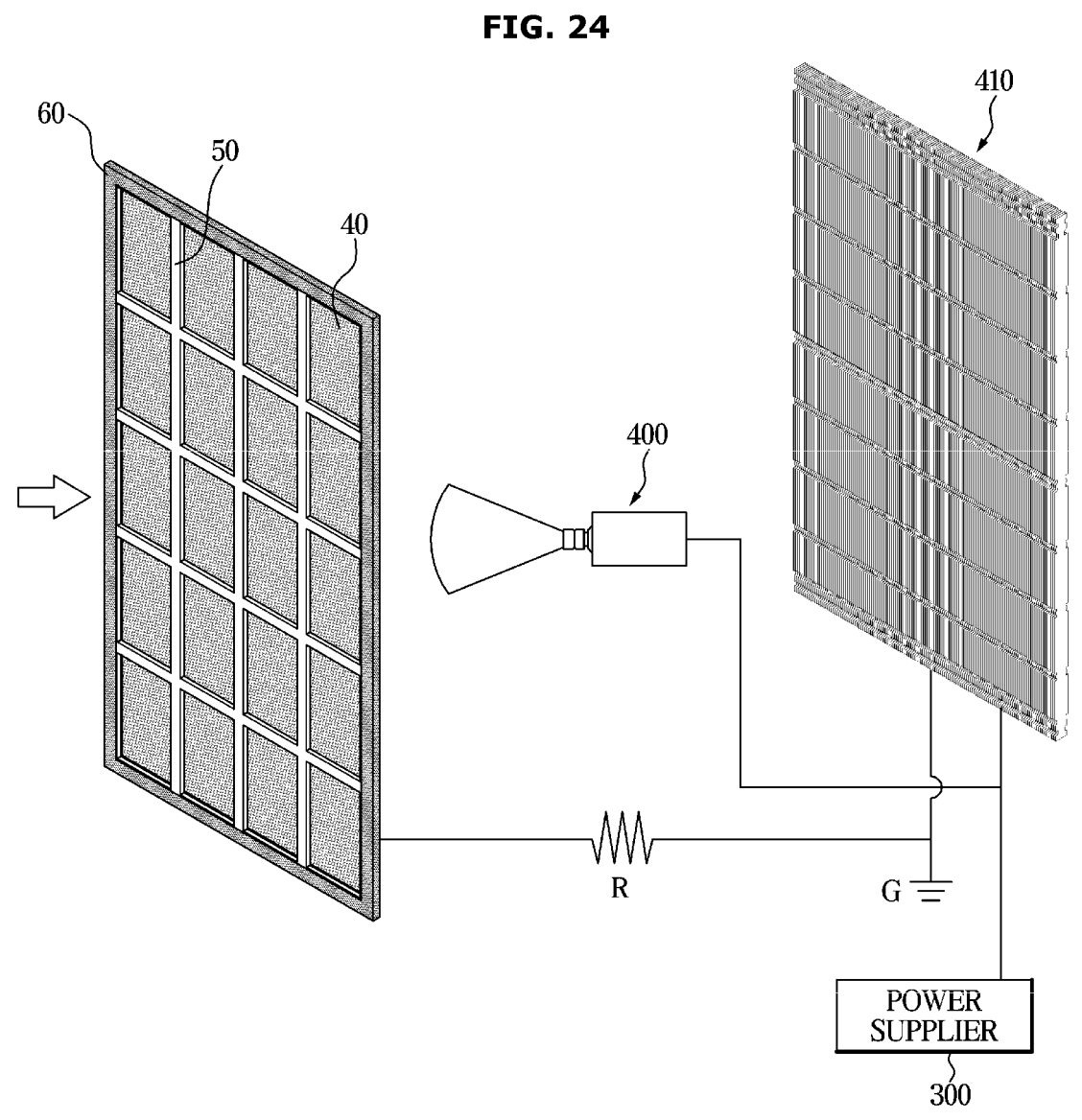

FIG. 24 is a view illustrating an electrostatic precipitator according to still another embodiment of the disclosure.

Referring to FIG. 24, a dust collecting sheet 10 may be replaced with a carbon brush electrode 400, to which a high voltage is applied, and a dust collecting filter 410 provided to collect an aerosol charged by the carbon brush electrode 400. The carbon brush electrode 400 may be connected to a power supplier 300, and the power supplier 300 may apply a high voltage to the carbon brush electrode 400. In response to a high voltage being applied to the carbon brush electrode 400, the carbon brush electrode 400 may be discharged to ionize molecules in the air, and emit the ions. The ions emitted by the carbon brush electrode 400 may charge the aerosol in the air.

The ions emitted from the carbon brush electrode 400 are diffused into space. The filter assembly 3 may be located upstream of the air flow path rather than the carbon brush electrode 400. The carbon brush electrode 400 and the filter assembly 3 may be spaced apart by a predetermined distance. As mentioned above, the filter assembly 3 may include at least one of a filter mesh 40 or a grille 50, and a conductive member 60 may be provided on a rim of the filter assembly 3.

FIG. 24 illustrates that the filter mesh 40, the grille 50 and the conductive member 60 are positioned upstream of the carbon brush electrode 400. The filter mesh 40, the grille 50, and the conductive member 60 may more effectively diffuse the ions emitted from the carbon brush electrode 400. Due to the electric field uniformly formed in the filter mesh 40 and the grille 50 by the conductive member 60, the ions may be evenly diffused over the entire region of the filter assembly 3. Accordingly, the charge amount of the aerosol may be increased.

The aerosol charged by the ions emitted by the carbon brush electrode 400 may be collected by the dust collecting filter 410 located downstream of an air flow path. The dust collecting filter 410 may form an electric field in response to a voltage being applied, and thus the charged aerosol may be attached to the dust collecting filter 410.

The dust collecting filter 410 may include a plurality of high-voltage electrodes and a plurality of low-voltage electrodes, like the dust collecting sheet 10 described above. However, because the carbon brush electrode 400 configured to generate ions is provided, an opening may not be provided in the high-voltage electrode and/or the low-voltage electrode of the dust collecting filter 410. That is, the dust collecting filter 410 may not generate ions.

Figure 25:
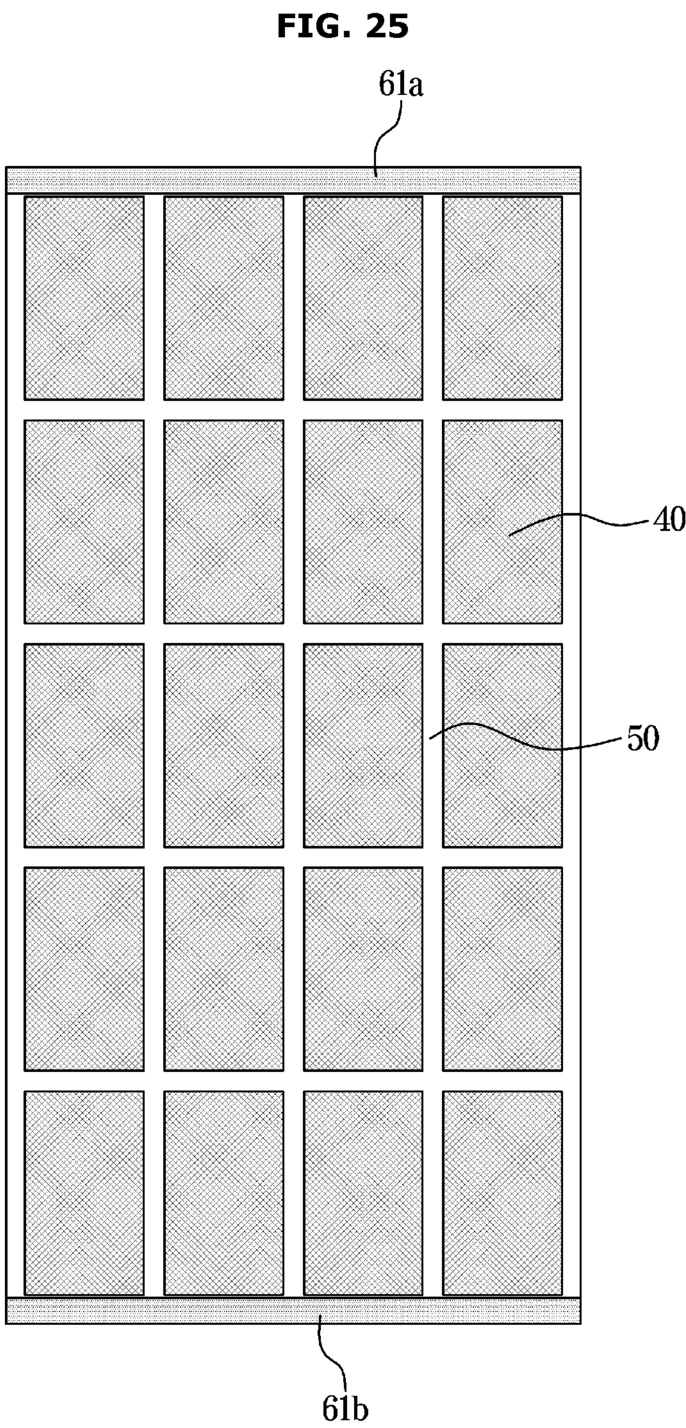
FIG. 25 is a view illustrating various embodiments in which the conductive member is symmetrically arranged.
Figure 26:
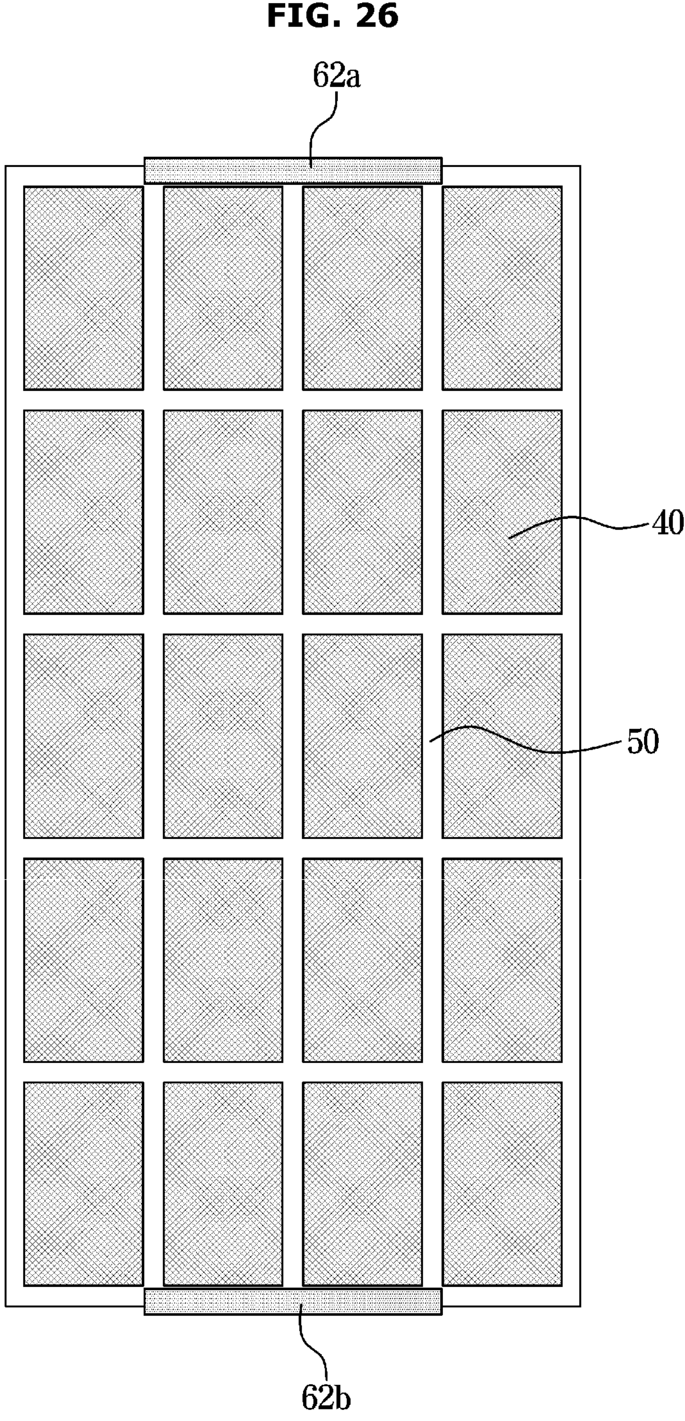
FIG. 26 is a view illustrating various embodiments in which the conductive member is symmetrically arranged.
Figure 27:
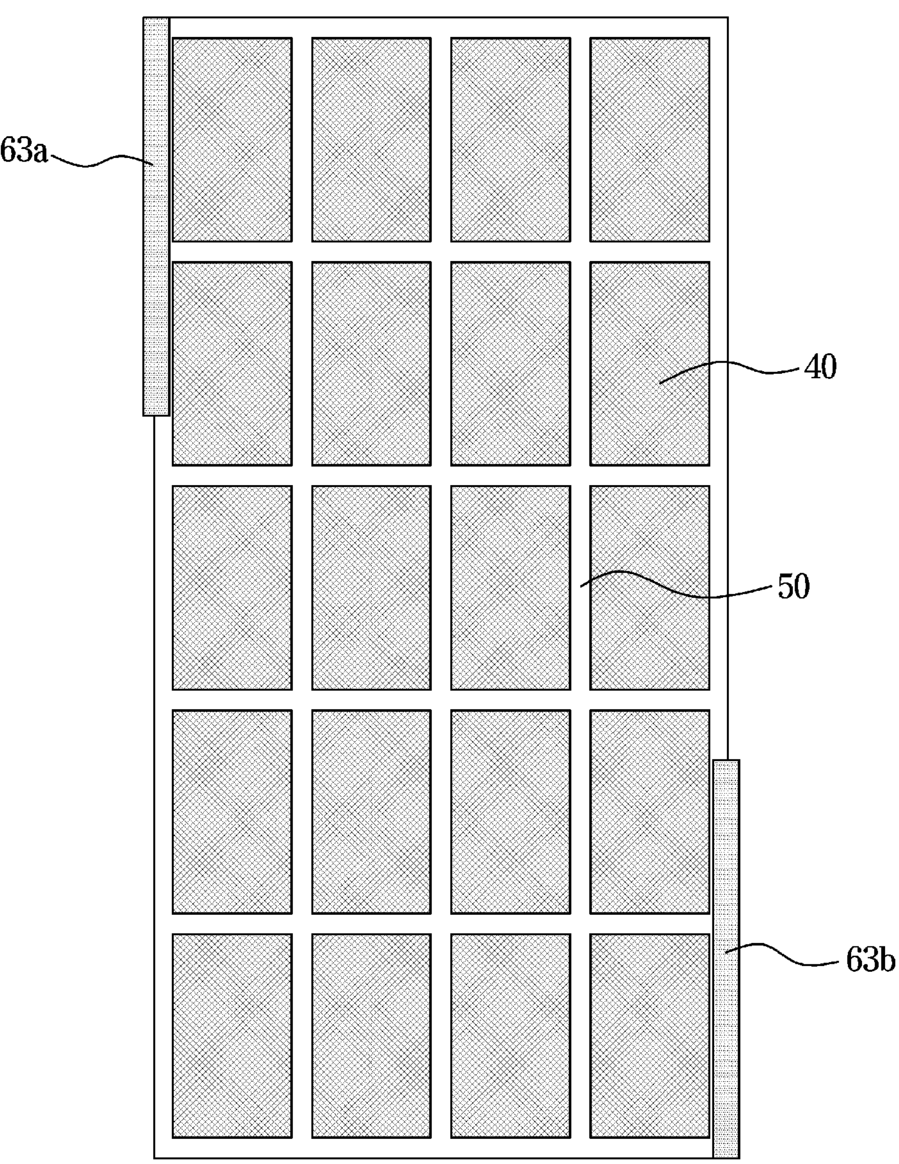
FIG. 27 is a view illustrating various embodiments in which the conductive member is symmetrically arranged.

FIGS. 25, 26, and 27 are views illustrating various embodiments in which the conductive member is symmetrically arranged.

Referring to FIG. 25, the conductive member 60 provided on the rim of plate-shaped structures 40 and 50 may be divided into a plurality. For example, each of conductive members 61*a* and 61*b* may be respectively arranged on a first side of the plate-shaped structures 40 and 50 and a second side thereof facing the first side. The conductive member 61*a* arranged on the first side and the conductive member 61*b* arranged on the second side may be symmetrical with respect to a centerline of the plate-shaped structures 40 and 50.

Referring to FIG. 26, a length of the conductive members 62*a* and 62*b* arranged on the first side and second side of the plate-shaped structures 40 and 50 may be less than a length of the first side and a length of the second side. Further, a length of the conductive member 62*a* arranged on the first side of the plate-shaped structures 40 and 50 may be different from a length of the conductive member 62*b* arranged on the second side of the plate-shaped structures 40 and 50.

Referring to FIG. 27, the conductive member 60 may include a first conductive member 63*a* arranged adjacent to a first vertex of the plate-shaped structures 40 and 50 and a second conductive member 63*b* arranged adjacent to a second vertex of the plate-shaped structures 40 and 50 arranged diagonally with respect to the first vertex. A first length of the first conductive member 63*a* and a second length of the second conductive member 63*b* may be less than the length of the one side of the plate-shaped structures 40 and 50. The first length of the first conductive member 63*a* may be different from the second length of the second conductive member 63*b*.

Figure 28:
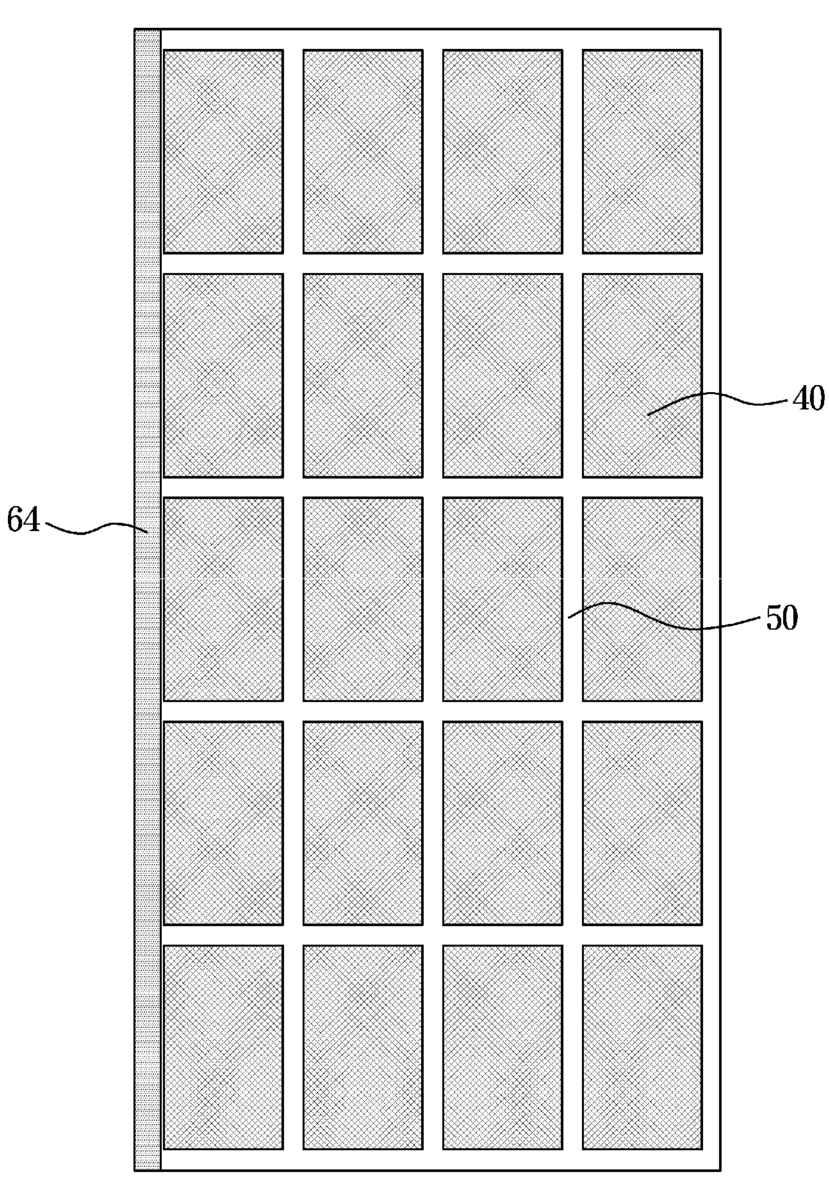
FIG. 28 is a view illustrating various embodiments in which the conductive member is asymmetrically arranged.
Figure 29:
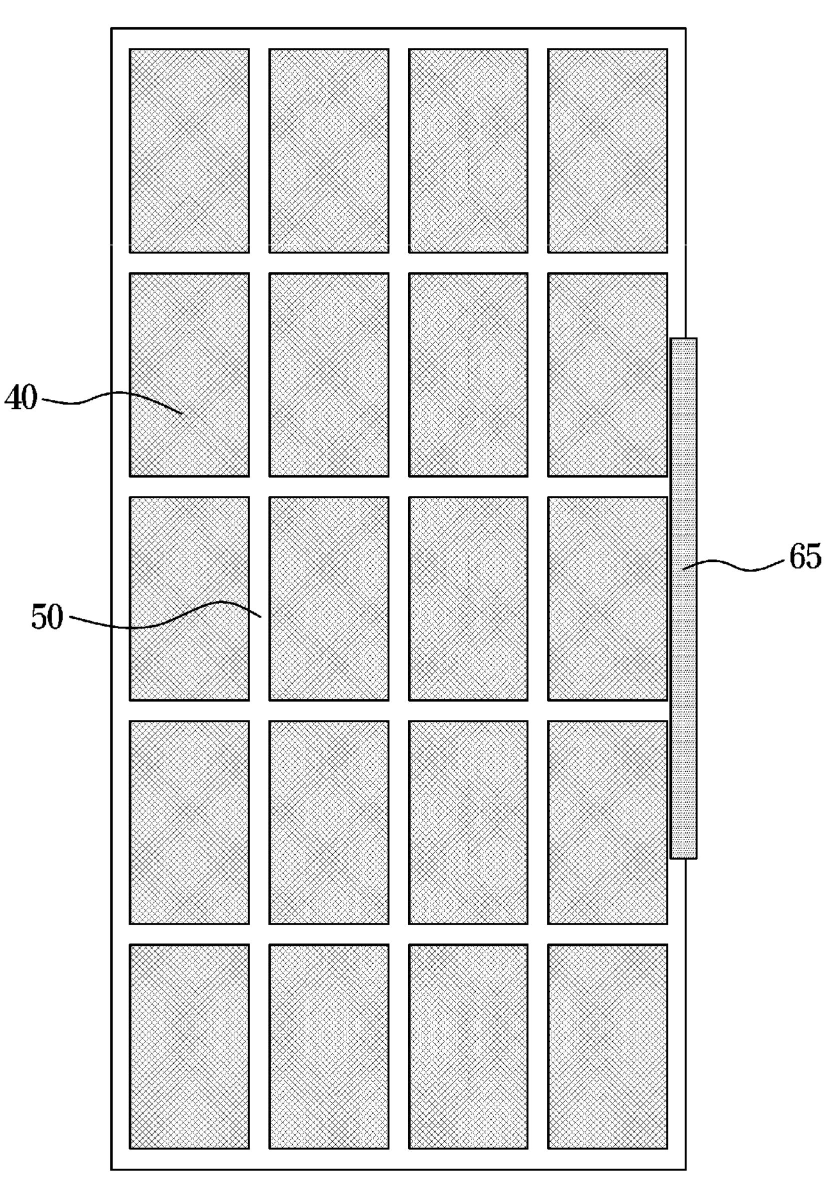
FIG. 29 is a view illustrating various embodiments in which the conductive member is asymmetrically arranged.
Figure 30:
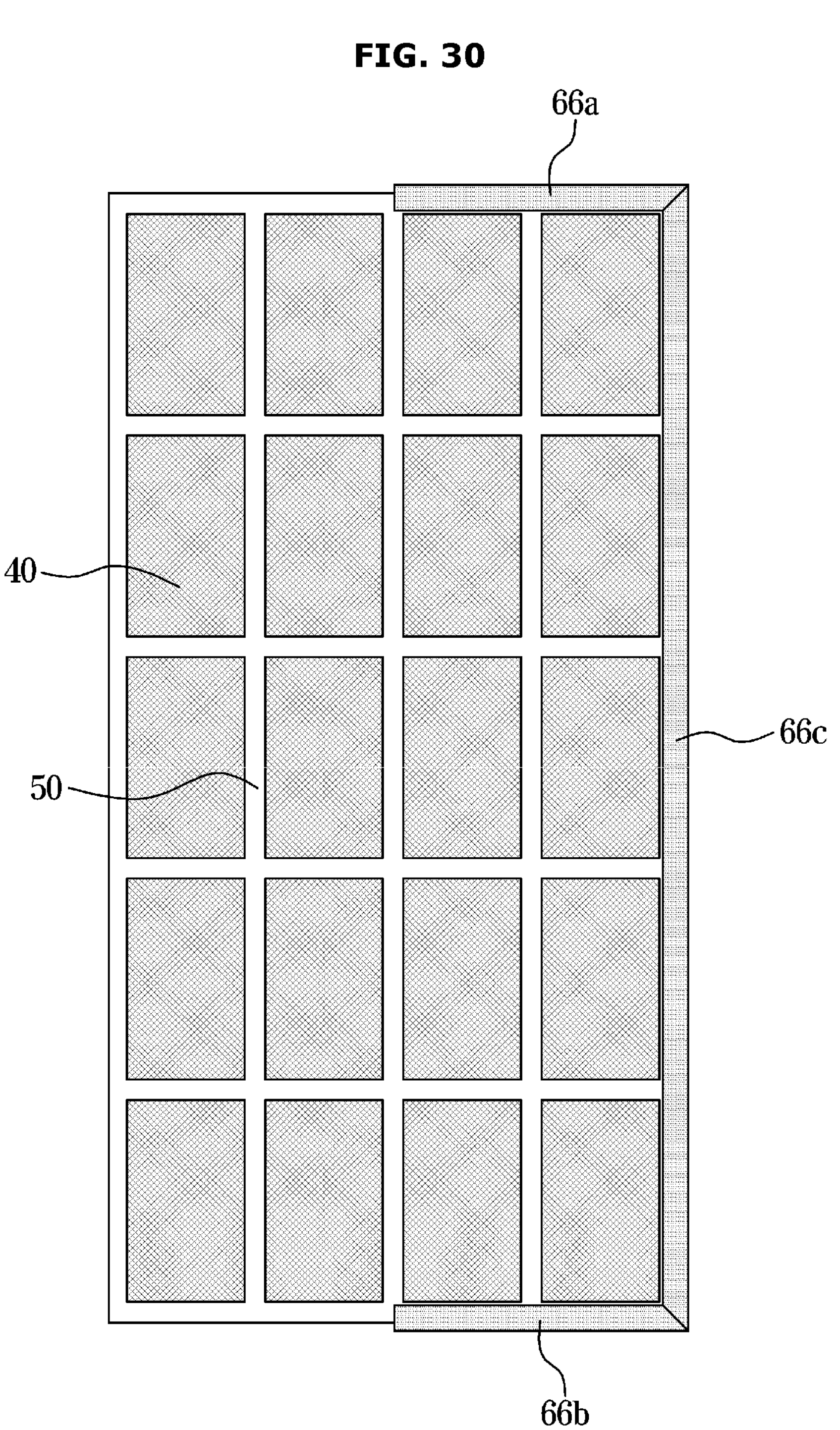
FIG. 30 is a view illustrating various embodiments in which the conductive member is asymmetrically arranged.

FIGS. 28, 29, and 30 are views illustrating various embodiments in which the conductive member is asymmetrically arranged.

Referring to FIGS. 28, 29, and 30, conductive members 64, 65, and 66 may be provided to have various lengths at a rim of the plate-shaped structures 40 and 50. As illustrated in FIGS. 28 and 29, the conductive members 64 and 65 may be formed on one side (for example, the left side or the right side). A length of the conductive member 64 shown in FIG. 28 may be the same as a length of one side of the plate-shaped structures 40 and 50. A length of the conductive member 65 shown in FIG. 29 may be less than the length of one side of the plate-shaped structures 40 and 50.

As shown in FIG. 30, conductive members 66*a*, 66*b*, and 66*c* may be provided on three sides of the plate-shaped structures 40 and 50. A conductive member 66*a* arranged on an upper side of the plate-shaped structures 40 and 50 may be referred to as an upper conductive member, a conductive member 66*b* arranged on a lower side may be referred to as a lower conductive member, and a conductive member 66*c* arranged on a right side may be referred to as a right conductive member. A length of the conductive members 66*a* and 66*b* arranged on the upper and lower sides of the plate-shaped structures 40 and 50 may be less than or equal to a length of the upper side and the lower side of the plate-shaped structures 40 and 50. A length of the conductive member 66*c* arranged on the right side may be less than or equal to a length of the right side of the plate-shaped structures 40 and 50.

As is apparent from the above description, an electrostatic precipitator may easily diffuse ions into an external space by arranging a structure provided to diffuse ions on an upstream side of an air flow path rather than a dust collecting sheet configured to generate ions.

Further, an electrostatic precipitator and a control method thereof may arrange a potential stabilizer configured to stabilize an electric potential, between a structure provided to diffuse ions and a ground, so as to allow an electric discharge to be smoothly performed in a high voltage electrode of a dust collecting sheet and simultaneously, to prevent the ions from accumulating on the structure.

Further, an electrostatic precipitator may arrange a conductive member at a rim of a structure provided to diffuse ions, so as to easily diffuse the ions generated by a dust collecting sheet.

A structure and a conductive member included in an electrostatic precipitator may form a uniform electric field to increase an amount of charge in an aerosol. In addition, even if the structure is arranged close to a dust collecting sheet, generation of sparks and discharge noise may be prevented. Accordingly, dust collection efficiency of the aerosol in the air may be increased.

Although a few embodiments of the disclosure have been shown and described, it would be appreciated by those skilled in the art that changes may be made in these embodiments without departing from the principles and spirit of the disclosure, the scope of which is defined in the claims and their equivalents.

What is claimed is:

1. An electrostatic precipitator comprising:

a dust collecting sheet configured to emit ions and configured to collect an aerosol charged by the ions from air flowing along an air flow path through the electrostatic precipitator;

a power supplier electrically connectable to the dust collecting sheet;

a plate-shaped structure arranged upstream of the dust collecting sheet along the air flow path, the plate-shaped structure comprising at least one of a filter mesh or a grille comprising a plurality of openings;

a potential stabilizer, arranged between the plate-shaped structure and a ground, to stabilize a potential of the plate-shaped structure, the potential stabilizer including a relay configured to connect to and disconnect from the plate-shaped structure and the ground; and a controller configured to control the relay to be repeatedly turned on and off at predetermined time intervals so that the plate-shaped structure and the ground are repeatedly connected and disconnected at the predetermined time intervals based on the power supplier supplying power to the dust collecting sheet.

2. The electrostatic precipitator of claim 1, wherein the controller is configured to set a closing time of the relay during which the relay is closed to be less than an opening time of the relay during which the relay is opened.

3. The electrostatic precipitator of claim 1 wherein the potential stabilizer further comprises a resistor-capacitor (RC) circuit connectable to the plate-shaped structure and connectable in parallel to the relay.

4. The electrostatic precipitator of claim 1, wherein the potential stabilizer comprises a resistance element.

5. The electrostatic precipitator of claim 1, wherein the plate-shaped structure is formed of a conductive material.

6. The electrostatic precipitator of claim 1, wherein the plate-shaped structure is formed of a semi-conductive material having a uniform resistance, or the plate-shaped structure comprises a first member formed of an insulator and a second member formed of a conductive material or a semi-conductive material.

7. The electrostatic precipitator of claim 6, further comprising:

a conductive member arranged on at least a portion of a rim of the plate-shaped structure.

8. The electrostatic precipitator of claim 7, wherein the conductive member having a bent shape to surround the rim of the plate-shaped structure.

9. The electrostatic precipitator of claim 7, wherein the conductive member is formed between the filter mesh and the grille.

10. The electrostatic precipitator of claim 7, wherein the plate-shaped structure is formed in a quadrangle, wherein the conductive member is arranged on a first side of the plate-shaped structure and a second side of the plate-shaped structure facing the first side symmetrically.

11. The electrostatic precipitator of claim 7, wherein the plate-shaped structure is formed in a quadrangle, wherein the conductive member comprises a first conductive member arranged adjacent to a first vertex of the plate-shaped structure and a second conductive member arranged adjacent to a second vertex of the plate-shaped structure arranged diagonally with respect to the first vertex, wherein a first length of the first conductive member and a second length of the second conductive member are less than a length of one side of the plate-shaped structure.

12. The electrostatic precipitator of claim 7, further comprising:

an insulating member arranged outside the conductive member to cover the conductive member.

13. The electrostatic precipitator of claim 1, wherein the dust collecting sheet comprises:

a plurality of high-voltage electrodes comprising a first dielectric layer and a first conductive electrode layer in which a part thereof is exposed to an outside through an opening of the first dielectric layer, the plurality of high-voltage electrodes to which a high-voltage is applied; and a plurality of low-voltage electrodes comprising a second dielectric layer and a second conductive electrode layer provided inside of the second dielectric layer, the plurality of low-voltage electrodes alternately arranged with the plurality of high-voltage electrodes, and to which a low-voltage is applied.

14. A control method of an electrostatic precipitator comprising a dust collecting sheet configured to collect an aerosol charged ions from air flowing along an air flow path through the electrostatic precipitator and a filter assembly arranged upstream of the dust collecting sheet along the air flow path, the control method comprising:

controlling a power supplier to supply power to the dust collecting sheet;

opening a relay of a potential stabilizer arranged between the filter assembly and a ground based on the power being supplied to the dust collecting sheet, the relay being configured to connect to and disconnect from the filter assembly and the ground; and controlling the relay to be repeatedly turned on and off at predetermined time intervals so that the plate-shaped structure and the ground are repeatedly connected and disconnected at the predetermined time intervals based on the power supplier supplying power to the dust collecting sheet.

* * * * *